United States Patent [19]

Fischli et al.

[11] Patent Number: 4,827,004
[45] Date of Patent: May 2, 1989

[54] ISOPRENE DERIVATIVES

[75] Inventors: Albert Fischli, Riehen; Max Schmid, Rheinfelden; Rudolf Schmid, Münchenstein, all of Switzerland

[73] Assignee: Hoffmann-La Roche Inc., Nutley, N.J.

[21] Appl. No.: 88,315

[22] Filed: Aug. 24, 1987

[30] Foreign Application Priority Data

Sep. 10, 1986 [CH] Switzerland .......................... 3649/86

[51] Int. Cl.$^4$ ............................................... C09F 5/00
[52] U.S. Cl. .................... 549/374; 260/399; 260/404; 260/405; 260/404.5; 544/158; 544/159; 544/164; 546/245; 548/530; 556/436; 556/437; 556/415; 556/419; 556/465; 562/577; 562/587; 562/560; 562/594; 564/268; 564/256; 564/203; 564/197; 564/198; 564/199; 560/261; 560/262; 568/376; 568/415; 568/596; 568/597; 568/598; 568/855; 568/857; 568/412; 568/31; 568/42; 568/32; 568/46
[58] Field of Search ............... 568/376, 415, 596, 597, 568/594, 855, 857, 412, 31, 42, 37, 46; 560/261, 262; 564/268, 256, 202, 197, 198, 199; 549/374; 562/577, 587, 560, 594; 556/437, 432, 415, 419, 465; 548/530; 546/245; 544/158, 159, 164; 260/399, 404.5, 404, 405

[56] References Cited

U.S. PATENT DOCUMENTS

| | | | |
|---|---|---|---|
| 3,453,317 | 7/1969 | Marbet et al. | 568/415 |
| 4,031,141 | 6/1977 | Hoffmann et al. | 568/415 |
| 4,192,953 | 3/1980 | Mishima et al. | 568/678 |

FOREIGN PATENT DOCUMENTS

| | | | |
|---|---|---|---|
| 0050853 | 5/1982 | European Pat. Off. | 568/415 |
| 0040407 | 11/1987 | European Pat. Off. | 568/415 |
| 2068370 | 8/1981 | United Kingdom | 568/647 |

OTHER PUBLICATIONS

Anderson, et al., J.A.C.S., 94, (1972), 5379.
Pratt et al., Dev. Endocrinol, 15, (1981), p. 107.
Yasuda et al., J.H.C.S., 96, (1974), 6513.
Columbo, J.C.S., Perkin I, (1982), 365.

Primary Examiner—James H. Reamer
Attorney, Agent, or Firm—Jon S. Saxe; George M. Gould; William H. Epstein

[57] ABSTRACT

Novel Isoprene Derivatives which have mucosa-protective and gastric acid secretion-inhibiting properties and are useful for combatting ulcers both by treating and as a prophylaxis against gastric and/or duodenal ulcers.

47 Claims, No Drawings

ISOPRENE DERIVATIVES

SUMMARY OF INVENTION

The present invention is concerned with isoprene derivatives. In particular, it is concerned with compounds of the general formula

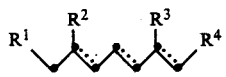

wherein
R$^1$ is a

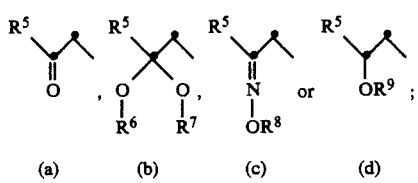

one of R$^2$ and R$^3$ is (C$_1$-C$_8$)-alkyl and the other is hydrogen or (C$_1$-C$_8$)-alkyl;
R$^4$ is a

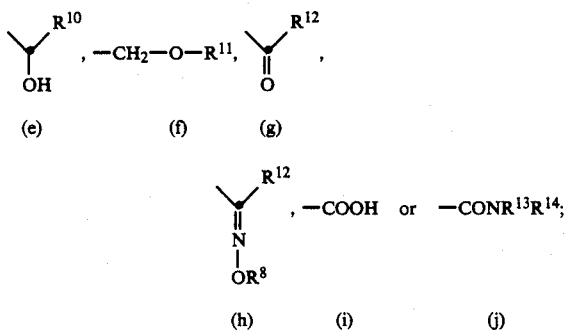

R$^5$ is a (C$_2$-C$_8$)-alkyl, other than isopropyl, (C$_3$-C$_8$)-cycloalkyl, (C$_2$-C$_8$)-alkenyl, (C$_2$-C$_8$)-alkynyl, tri-(C$_1$-C$_8$)-alkyl-silylethynyl or, when R$^1$ is (a), R$^5$ can also be

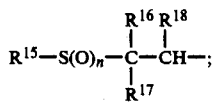

R$^6$ and R$^7$ are individually (C$_1$-C$_8$)-alkyl or taken together form a di- or trimethylene group optionally substituted by one or two (C$_1$-C$_8$)-alkyl, (C$_1$-C$_8$)-alkoxy-(C$_1$-C$_8$)alkyl or (C$_1$-C$_8$)-alkoxycarbonyl groups;
R$^8$ is hydrogen or (C$_1$-C$_8$)-alkyl;
R$^9$ is hydrogen or (C$_2$-C$_8$)-alkanoyl;
R$^{10}$ is (C$_1$-C$_8$)-alkyl;
R$^{11}$ is hydrogen, (C$_1$-C$_8$)-alkyl, (C$_2$-C$_8$)-alkanoyl or a

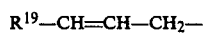  (l)

or

  (m);

R$^{12}$ is hydrogen, (C$_1$-C$_8$)-alkyl, (C$_2$-C$_8$)-alkenyl or (C$_2$-C$_8$)-alkynyl;
R$^{13}$ and R$^{14}$ are individually hydrogen or (C$_1$-C$_8$)-alkyl or taken together with the attached nitrogen atom form 1-pyrrolidinyl, piperidino or morpholino;
R$^{15}$ is (C$_1$-C$_8$)-alkyl, (C$_2$-C$_8$)-alkanoyl, (C$_1$-C$_8$)-alkoxycarbonyl-(C$_1$-C$_8$)-alkyl, hydroxy-(C$_2$-C$_8$)-alkyl, (C$_2$-C$_8$)-alkanoyloxy-(C$_2$-C$_8$)-alkyl, (C$_2$-C$_8$)-alkanoylamino-(C$_2$-C$_8$)-alkyl or (C$_2$-C$_8$)-alkyl disubstituted by (C$_2$-C$_8$)-alkanoylamino and (C$_1$-C$_8$)-alkoxycarbonyl or by (C$_2$-C$_8$)-alkanoyloxy and (C$_1$-C$_8$)-alkoxycarbonyl; n is the number 0, 1 or 2;
R$^{16}$, R$^{17}$ and R$^{18}$ individually are hydrogen or (C$_1$-C$_6$)-alkyl containing in total a maximum of 6 C-atoms;
R$^{19}$ is hydrogen or (C$_1$-C$_5$)-alkyl; each of the dotted lines designates an optional additional C—C bond having the E- or Z- configuration; and
the double bond present in the residues of formulae (c) and (h) has the E- or Z- configuration;
as well as pharmaceutically acceptable salts of acidic compounds of formula I with bases.

These compounds are novel with the exception of 10-hydroxy-3,7,11-trimethyl-2,6,11-dodecatrienoic acid and 3,7,11-trimethyl-2,6,11-dodecatriene-1,10-diol. It has been found that these novel compounds as well as 10-hydroxy-3,7,11-trimethyl-2,6,11-dodecatrienoic acid and 3,7,11-trimethyl-2,6,11-dodecatriene-1,10-diol possess valuable pharmacodynamic properties, namely gastric acid secretion-inhibiting and/or mucosa-protective properties, so that they can be used for the control or prevention of illnesses of the gastrointestinal tract, especially against gastric ulcers and duodenal ulcers.

The compound 10-hydroxy-3,7,11-trimethyl-2,6,11-dodecatrienoic acid has been described as a juvenile hormone agent. Dev Endocrinol. (Amsterdam) 15 (Juv. Horm. Biochem) 107 (1981). The compound 3,7,11-trimethyl-2,6,11-dodecatrien-1,10-diol has also been described as a juvenile hormone agent. See J. Am. Chem. Soc. 96, 6513 (1974) and Bull. Chem. Soc. Japan 52 (1701) (1979). Furthermore, Great Britain application No. 2,068,370 and European applications Nos. 0,040,407 and 0,050,853 disclose isopropyl derivatives of isoprene compounds.

Objects of the present invention are the compounds and salts defined earlier as therapeutically active substances, medicaments containing such a compound or a salt thereof, the manufacture of such medicaments, the use of the compounds and salts defined earlier in the control or prevention of illnesses, especially in the control or prevention of gastric ulcers and duodenal ulcers, or the use of the compounds and salts defined earlier for the manufacture of medicaments for the control or prevention of gastric ulcers and duodenal ulcers, as well as the novel compounds and salts defined earlier per se and the manufacture of these novel compounds and salts.

DETAILED DESCRIPTION

The term "alkyl" taken alone or in combinations such as "alkoxyalkyl" or "hydroxyalkyl" denotes straight-chain or branched saturated hydrocarbon residues such as methyl, ethyl, n-propyl, sec-butyl, t-butyl and the like. The term "alkoxy" denotes alkyl groups in the sense of the previous definition attached via an oxygen atom.

The term "cycloalkyl" embraces cycloaliphatic residues such as cyclopropyl, cyclobutyl, cyclopentyl, cyclohexyl and the like. The terms "alkenyl" and "alkynyl" denote hydrocarbon residues which contain a carbon-carbon double or triple bond such as e.g. vinyl, 1-methylvinyl, 1-propenyl, 2-methyl-1-propenyl, ethynyl and the like.

The term "alkanoyl" denote residues such as acetyl, propionyl and the like. The terms "alkoxycarbonyl" and "alkoxycarbonylalkyl" denotes residues such as methoxy carbonyl or methoxycarbonylmethyl and the like. The term "hydroxyalkyl" denotes residues such as 2-hydroxyethyl. The terms "alkanoyloxyalkyl" and "alkanoylaminoalkyl" denote residues such as acetoxymethyl or 2-acetylaminoethyl and the like.

Among the compounds of formula I defined earlier there are preferred those in which $R^1$ signifies a residue of formula (a), (b), (c) or (d), $R^2$ and $R^3$ each signify ($C_1$–$C_8$)-alkyl, $R^4$ signifies a residue of formula (f), (g), (h), (i) or (j), $R^5$ signifies ($C_2$–$C_8$)-alkenyl, ($C_2$–$C_8$)-alkynyl or tri-($C_1$–$C_8$)-alkylsilyl-ethynyl, $R^6$ and $R^7$ each signify ($C_1$–$C_8$)-alkyl or together signify the dimethylene group. $R^8$ signifies hydrogen or ($C_1$–$C_8$)-alkyl, $R^9$ signifies hydrogen, $R^{11}$ signifies hydrogen or ($C_2$–$C_8$)-alkanoyl, $R^{12}$, $R^{13}$ and $R^{14}$ each signify hydrogen and two of the dotted lines signify non-conjugated additional C—C bonds; of these compounds there are especially preferred those in which $R^2$ and $R^3$ each signify methyl, $R^5$ signifies vinyl, 1-methylvinyl, 1-propenyl, 2-methyl-1-propenyl, ethynyl, 1-propynyl or trimethylsilylethynyl, $R^6$ and $R^7$ each signify methyl or ethyl or together signify the dimethylene group, $R^8$ signifies hydrogen or methyl and $R^{11}$ signifies hydrogen or acetyl, especially those in which $R^1$ signifies a residue of formula (a) and $R^4$ signifies a residue of formula (f).

Particularly preferred compounds of formula I are:
(all-E)-12-Hydroxy-6,10-dimethyl-6,10-dodecadien-1-yn-3-one;
(all-E)-12-hydroxy-6,10-dimethyl-1,6,10-dodecatrien-3-one;
(all-E)-13-hydroxy-7,11-dimethyl-7,11-tridecadien-2-yn-4-one;
(all-E)-13-hydroxy-7,11-dimethyl-2,7,11-tridecatrien-4-one; and
(all-E)-10,10-diethoxy-3,7-dimethyl-2,6-dodecadien-11-yn-1-ol.

Likewise especially preferred compounds of formula I are:
(all-E)-12-Hydroxy-2,6,10-trimethyl-1,6,10-dodecatrien-3-one;
(all-E)-10-oxo-3,7,11-trimethyl-2,6,11-dodecatrienal; and
(6Z,10Z)-12-hydroxy-2,6,10-trimethyl-1,6,10-dodecatrien-3-one.

Further preferred compounds of formula I are:
(all-E)-3,7-Dimethyl-9-[2-(1-methylvinyl)-1,3-dioxolan-2-yl]-2,6-nonadien-1-ol;
(E,E)-3,7,11-trimethyl-10-oxo-2,6,11-dodecatrienamide;
(all-E)-13-hydroxy-2,7,11-trimethyl-2,7,11-tridecatrien-4-one;
(6E,10Z)-12-hydroxy-2,6,10-trimethyl-1,6,10-dodecatrien-3-one; and
(6E,10E)-12-hydroxy-2,6,10-trimethyl-1,6,10-dodecatrien-3-one.

Further representative compounds of formula I are:
(all-E)-10-Oxo-3,7,11-trimethyl-2,6,11-dodecatrienoic acid;
(all-E)-10,10-dimethoxy-3,7,11-trimethyl-2,6,11-dodecatrien-1-ol;
(all-E)-10-hydroxy-3,7,11-trimethyl-2,6,11-dodecatrienal;
(all-E)-12-hydroxy-6,10-dimethyl-1-(trimethylsilyl)-6,10-dodecadien-1-yn-3-one;
(2E,6E)-3,7,11-trimethyl-10-oxo-2,6,11-dodecatrienal (E/Z)-oxime;
(6E,10E)-12-hydroxy-6,10-dimethyl-6,10-dodecadien-1-yn-3-one (E/Z)-O-methyl oxime; and
(2E,6E,11(E/Z))-3,7-dimethyl-2,6,11-tridecatriene-1,10-diol.

The novel compounds of formula I defined earlier and their salts can be manufactured in accordance with the invention by (a) cleaving off the protecting group(s) from a compound of the general formula

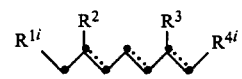

II wherein $R^{1i}$ signifies a residue of formula (a), (b) or (c) defined earlier or a residue of the formula

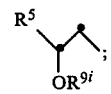

(d$^i$)

$R^{4i}$ signifies a residue of formula (g), (h), (i) or (j) defined earlier or a residue of the formula

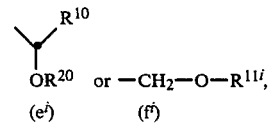

(e$^i$)  (f$^i$)

$R^{9i}$ signifies hydrogen, ($C_2$–$C_8$)-alkanoyl or a protecting group, $R^{11i}$ signifies hydrogen, ($C_1$–$C_8$)-alkyl, ($C_2$–$C_8$)-alkanoyl, a group of formula (l) or (m) defined earlier or a protecting group and $R^{20}$ signifies hydrogen or a protecting group and $R^2$, $R^3$, $R^5$, $R^{10}$ and the dotted line have the significance given earlier, with the proviso that the molecule contains at least one protecting group;

or (b) opening the epoxide ring in a compound of the general formula

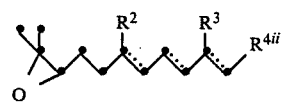

III wherein $R^{4ii}$ signifies a residue of formulae (f), (h), (i) or (j) defined earlier and $R^2$, $R^3$ and the dotted lines have the significance given earlier;

or (c) reducing a carboxylic acid ester of the general formula

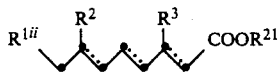   IV wherein $R^{1ii}$ is a residue of formula (b) defined earlier or a residue of the formula

   (d$^{ii}$)

and $R^{21}$ is $(C_1-C_8)$-alkyl and $R^2$, $R^3$, $R^5$ and the dotted lines have the significance given earlier,
to the corresponding primary alcohol; or (d) hydrolyzing a carboxylic acid ester of the general formula

   V wherein $R^{1iii}$ signifies a residue of formula (b) or (c) defined earlier or of formula (d$^{ii}$) above or of the formula

   (a$^i$)

$R^{5i}$ signifies $(C_2-C_8)$-alkyl, but not isopropyl, $(C_3-C_8)$-cycloalkyl, $(C_2-C_8)$-alkenyl, $(C_2-C_8)$-alkynyl or tri-$(C_1-C_8)$-alkyl-silylethynyl, $R^{21}$ has the above significance and $R^2$, $R^3$ and the dotted lines have the significance given earlier,
to the corresponding carboxylic acid; or (e) in a compound of formula I defined earlier in which $R^1$ signifies a residue of formula (b), (c) or (d) defined earlier or a residue of formula (a$^i$) above, with the proviso that the molecule contains at least one hydroxy group attached to a C-atom, oxidizing this (these) hydroxy group(s) or a thereof to (an) oxo group(s); or (f) treating a compound of general formula I defined earlier in which $R^1$ signifies a residue of formula (b) or (d) defined earlier and $R^4$ signifies a formyl group with a Grignard reagent yielding a $(C_1-C_8)$-alkyl group, a $(C_2-C_8)$-alkenyl group or a $(C_2-C_8)$-alkynyl group; or (g) reacting a compound of formula I defined earlier in which $R^1$ is a residue of formula (b), (c) or (d) defined earlier or a residue of formula (a$^i$) above, with the proviso that the molecule contains at least one oxo group, with a compound of the general formula $$H_2N-OR^8 \qquad VI$$

wherein $R^8$ is as above;
or (h) reacting a compound of formula I defined earlier in which $R^1$ is a residue of the formula

   (a$^{ii}$)

$R^4$ is a residue of formula (e), (h), (i) or (j) defined earlier or a residue of formula (f$^i$) above and $R^{5ii}$ signifies $(C_2-C_8)$-alk-1-enyl,
with a compound of the general formula $$R^{15}-S-H \qquad VII$$

wherein $R^{15}$ has the significance given earlier;
or (i) in a compound of formula I defined earlier in which $R^1$ signifies a residue of the formula

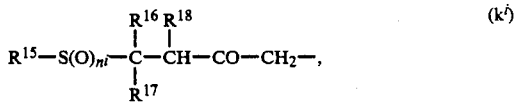   (k$^i$)

and $n^i$ is the number 0 or 1 and $R^{15}$, $R^{16}$, $R^{17}$ and $R^{18}$ are as above;
oxidizing the mercapto group to the sulfinyl or sulfonyl group or oxidizing the sulfinyl group to the sulfonyl group; or (j) in a compound of formula I defined earlier in which $R^1$ signifies a residue of formula (a), (b) or (d) defined earlier or a residue of the formula

   (c$^i$)

$R^4$ is a residue of formula (e), (f), (g), (i) or (j) defined earlier or a residue of the formula

   (h$^i$)

and $R^{8i}$ is $(C_1-C_8)$-alkyl and $R^5$ and $R^{12}$ are as above, with the proviso that the molecule contains at least one hydroxy group, acylating this (these) hydroxy group(s) with an agent yielding a $(C_2-C_8)$-alkanoyl residue; whereupon, if desired, a resulting acidic compound of formula I defined earlier is converted into a pharmaceutically usable salt with a base.

As protecting groups in the compounds of general formula II, which are used as starting products in process variant (a), there are, of course, suitable only those which can be cleaved off by methods which selectively remove these protecting groups without affecting other structural elements present in the molecule. The removal of the protecting group or of the protecting groups from the compounds of general formula II is effected according to methods known per se, whereby, of course, the nature of the protecting group or protecting groups to be removed must be taken into consideration when choosing the method to be used and care muxt be taken that only the protecting group or protecting groups is/are selectively removed without affecting other structural elements present in the molecule.

Suitable protecting groups are, for example, readily cleavable acetal and ketal protecting groups such as tetrahydro-2H-pyran-2-yl, methoxymethyl, methoxyethoxymethyl, 1-methoxy-1-methylethyl and the like; readily cleavable metal-organic groups, especially trialkylsilyl groups such as t-butyldimethylsilyl, trimethylsilyl, triisopropylsilyl and the like or alkyldiarylsilyl groups such as t-butyldiphenylsilyl and the like; etc.

Methods for the removal of the residues which have been mentioned previously as examples of protecting groups are described in the literature and are accordingly familiar to any person skilled in the art. For example, a heterocyclic group such as 2-tetrahydropyranyl or an alkoxyalkyl group such as methoxymethyl can be cleaved off readily by bringing the compound of formula II into contact with an acid. Preferred acids are organic acids such as formic acid, acetic acid, propionic acid and p-toluenesulphonic acid and inorganic acids such as hydrochloric acid and sulphuric acid. The reaction is carried out in the presence or absence of a solvent. A solvent is, however, preferably used in order to carry out the reaction in a mild manner. Preferred solvents are water, an alcohol such as methanol and ethanol and a mixture of water and one of these alcohols. No special restrictions exist with respect to the reaction temperature, although room temperature is preferred. The cleavage of a tetrahydro-2H-pyran-2-yl group is effected especially by means of pyridinium p-toluenesulfonate, conveniently in aqueous tetrahydrofuran or in an alcoholic system, e.g. in absolute ethanol or in aqueous (e.g. 90%) ethanol; if $R^{1i}$ in formula II signifies a residue of formula (a) above, then when the reaction is carried out in an anhydrous alcoholic system, partial or complete ketalization can occur and there is obtained, at least partially, a corresponding compound of formula I in which $R^1$ signifies a residue of formula (b) defined earlier.

The cleavage of a tetrahydro-2H-pyran-2-yl group can also be effected, for example, by means of an acidic ion-exchanger, e.g. by means of Dowex 50 WX8, whereby the cleavage is conveniently carried out in an alcoholic system, e.g. in methanol.

A silyl protecting group such as trimethylsilyl can be cleaved off readily by bringing the compound II into contact with water or an aqueous solution of an acid or base. As acids and bases there can be mentioned organic acids, e.g. formic acid, acetic acid and propionic acid, and inorganic acids, e.g. hydrochloric acid and sulphuric acid, or inorganic bases such as the hydroxide of an alkali metal or of an alkaline earth metal, e.g. potassium hydroxide and calcium hydroxide, and the carbonate of an alkali metal or of an alkaline earth metal, e.g. potassium carbonate and calcium carbonate. No special restriction exists with respect to the reaction temperature, but in general room temperature is preferably used. The time required for the removal of the protecting group varies depending on the type of protecting group. The silyl protecting groups can also be cleaved off with fluoride-containing reagents, for example by means of tetrabutylammonium fluoride in tetrahydrofuran or by means of silver fluoride in water.

The opening of the epoxide ring in a compound of general formula III in accordance with process variant (b) is also effected according to methods which are known per se and which are familiar to any person skilled in the art. For example, the compound of formula III in an aromatic hydrocarbon such as toluene or the like can be heated, conveniently at reflux, with aluminum isopropylate. The opening of the epoxide ring can also be effected with amide reagents such as e.g. lithium diethylamide, lithium diisopropylamide and the like in ether or hexane or with diethylaluminium-2,2,6,6-tetramethylpiperidine in benzene.

The reduction of a carboxylic acid ester of general formula IV in accordance with process variant (c) is also effected according to methods which are known per se and which are familiar to any person skilled in the art. There is conveniently used as the reduction agent a complex metal hydride such as diisobutylaluminium hydride, lithium aluminum hydride or sodium dihydrobis[2-methoxyethoxy]aluminate in an organic solvent which is inert under the reaction conditions, for example in a hydrocarbon such as hexane, toluene and the like or in an ether such as diethyl ether, tetrahydrofuran and the like.

The hydrolysis of a carboxylic acid ester of general formula V in accordance with process variant (d) is also effected according to methods which are known per se and which are familiar to any person skilled in the art. Depending on the structure of the starting material, i.e. of the carboxylic acid ester of general formula V, this hydrolysis is carried out under alkaline conditions or under acidic conditions. An alkaline hydrolysis is conveniently effected by means of a strong inorganic base, for example an alkali metal hydroxide such as sodium hydroxide or the like in a suitable solvent system, for example in water or aqueous dioxan or the like. An acidic hydrolysis is conveniently effected with mineral acids such as hydrochloric acid or the like in a suitable solvent system, for example in aqueous tetrahydrofuran or the like.

The oxidation in accordance with process variant (e) is effected according to methods which are known per se and which are familiar to any person skilled in the art for the conversion of hydroxy groups into oxo groups. As the oxidation agent there is conveniently used manganese dioxide (pyrolusite) in a suitable solvent which is inert under the reaction conditions, for example in a hydrocarbon such as hexane or the like, in a halogenated hydrocarbon such as methylene chloride or the like, etc. If the starting material contains two hydroxy groups, of which one is primary and the other is secondary, then, if desired, by suitable choice of the reaction conditions the primary hydroxy group can be selectively oxidized without affecting the secondary hydroxy group. In place of manganese dioxide there can also be used chromium-containing oxidation agents such as e.g. pyridinium dichromate or pyridinium chlorochromate and the like. As solvents there are usually used halogenated hydrocarbons such as methylene chloride and the like; for pyridinium dichromate there can also be used dimethylformamide. Chromium trioxide in sulphuric acid (Jones reagent) is a further common oxidation agent.

The Grignard reaction is accordance with process variant (f) is also effected according to methods which are known per se and which are familiar to any person skilled in the art. As the Grignard reagent there are conveniently used compounds such as methylmagnesium iodide, vinyl-magnesium bromide, n-pentylmagnesium bromide, cyclopropyl-lithium or the like; as solvents there are suitable, for example, ethers such as diethyl ether or tetrahydrofuran and the like. When $R^1$ in the starting material signifies a residue of formula (d) and $R^9$ signifies $(C_2–C_8)$-alkanoyl, then this alkanoyl group is cleaved off in the course of the Grignard reaction and there is obtained a corresponding compound of formula I in which $R^1$ signifies a residue of formula (d) and $R^9$ signifies hydrogen.

The oxime formation in accordance with process variant (g) is also effected according to methods which are known per se and which are familiar to any person skilled in the art. Conveniently, the compound of formula VI (e.g. hydroxylamine, O-methylhydroxylamine or the like) is used in the form of an acid addition salt, for example as the hydrochloride; in this case the reaction is effected in the presence of a base, e.g. an alkali metal hydroxide such as sodium hydroxide and the like, an alkali metal salt of a weak acid such as sodium acetate and the like, etc. As the solvent there is conveniently used an alcoholic or alcoholic/aqueous system, for example absolute methanol, aqueous methanol or the like.

For the reaction in accordance with process variant (h) there is used as the sulfur-containing component a compound of formula VII such as 2-mercaptoethanol, methyl thioglycolate, thioacetic acid or the like or a protected derivative of a compound of formula VII such as N-(2-acetylthioethyl)acetamide, S-[(2-acetamido-2-methylcarbonyl)ethyl]thioacetate or the like; the protecting group is cleaved off from such protected derivatives under the reaction conditions, whereby the corresponding compound of formula VII is liberated and reacted in situ. The reaction is conveniently effected in the presence of a base, for example a tertiary organic base such as triethylamine or the like, and in a suitable organic solvent which is inert under the reaction conditions, for example in an alcohol such as methanol or the like, in a halogenated hydrocarbon such as methylene chloride or the like, etc.

For the oxidation in accordance with process variant (i), in which a mercapto group is oxidized to the sulfinyl or sulfonyl group or a sulfinyl group is oxidized to the sulfonyl group, there are used oxidation agents which are customary for such conversions, for example peracids such as m-chlorperbenzoic acid, hydrogen peroxide, peresters, sodium metaperiodate etc. The oxidation is conveniently effected in an organic solvent which is inert under the reaction conditions, for example in a halogenated hydrocarbon such as methylene chloride, chloroform, dichloroethane and the like or in a hydrocarbon such as benzene and the like; when hydrogen peroxide is used as the oxidation agent, the oxidation can also be carried out in acetic acid, aqueous acetic acid and the like. It is advantageous to use the oxidation agent in slight excess with respect to the compound to be oxidized. The oxidation is conveniently carried out at room temperature or thereunder, preferably at temperatures of about −50° to about 0° C.

As O-acylating agents in process variant (j) there are used reactive functional derivatives of $(C_2-C_8)$-alkanecarboxylic acids, conveniently corresponding acid chlorides or acid anhydrides such as acetic anhydride or the like. The acylation is effected in the presence of a base, conveniently a tertiary organic base such as pyridine, triethylamine, N-methylpiperidine, 4-dimethylaminopyridine or the like. Suitable solvents are primarily halogenated hydrocarbons such as methylene chloride or the like; where pyridine is used as the base, then this can simultaneously also serve as the solvent.

The conversion of an acidic compound of formula I obtained into a pharmaceutically usable salt can be carried out by treatment with a pharmaceutically acceptable base in a manner known per se. As such salts there are suitable not only those with cations derived from an inorganic base, e.g. potassium salts, calcium salts and the like, but also salts with organic bases such as ethylenediamine, monoethanolamine, diethanolamine and the like.

The preparation of the starting materials of general formula II, III, IV and V can be effected starting from known compounds according to methods which are known per se and which are familiar to any person skilled in the art. The preparation of such compounds is illustrated in the following Schemes 1 to 5 on the basis of selected specific cases. The abbreviations occurring in these Schemes have the following significances:

DHP=3,4-Dihydro-2H-pyran
DIBAH=Diisobutylaluminium hydride
OTHP=(Tetrahydro-2H-pyran-2-yl)oxy
PTS=Pyridinium p-toluenesulfonate.

Schemes 1 to 3 relate to the preparation of compounds of formula II, Scheme 4 relates to the preparation of compounds of formula III and Scheme 5 relates to the preparation of compounds of formulae IV and V.

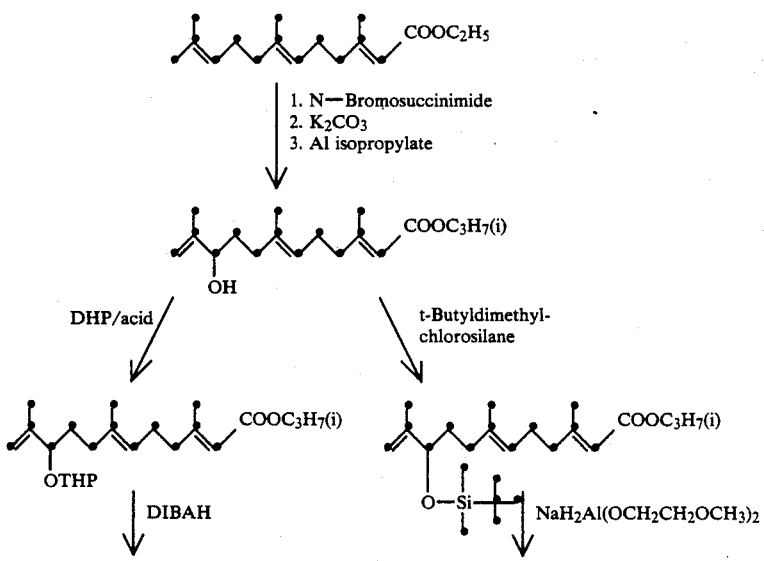

-continued
Scheme 1
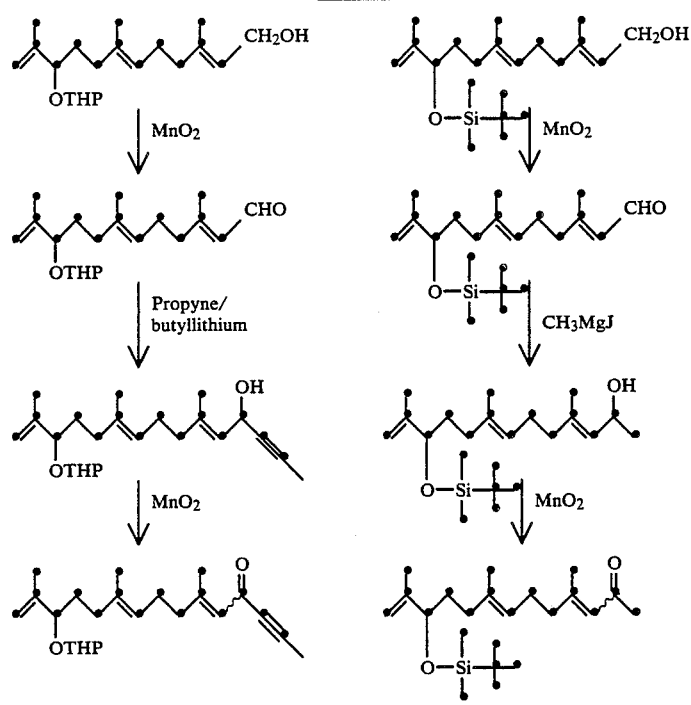
Scheme 2
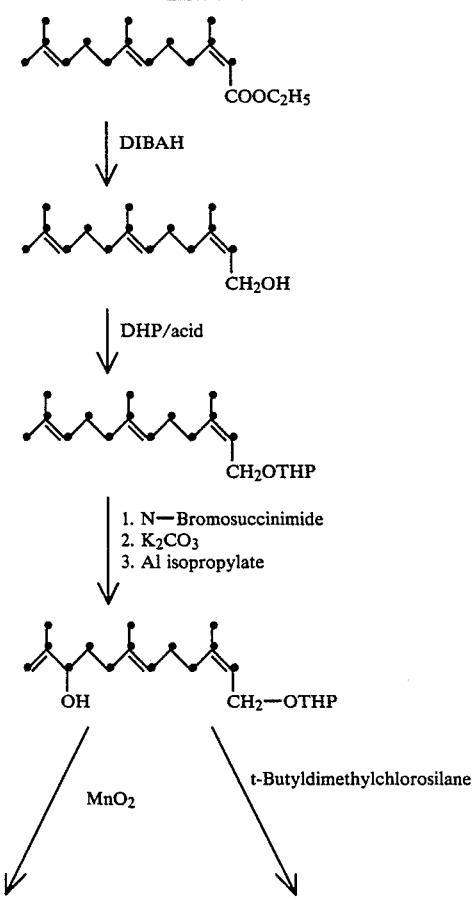

-continued
Scheme 2
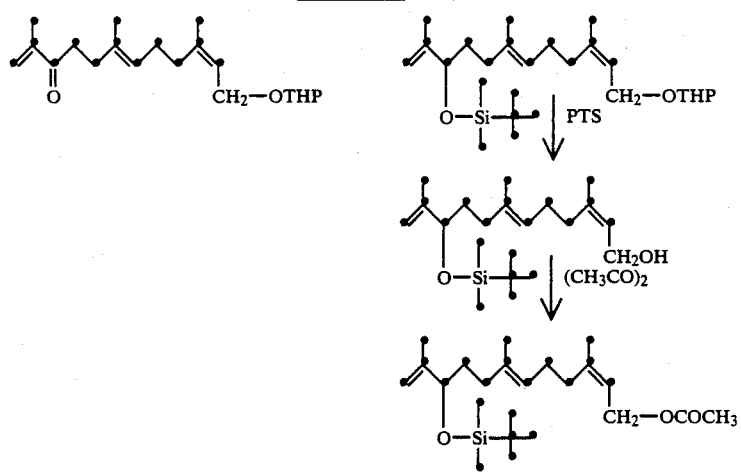
Scheme 3
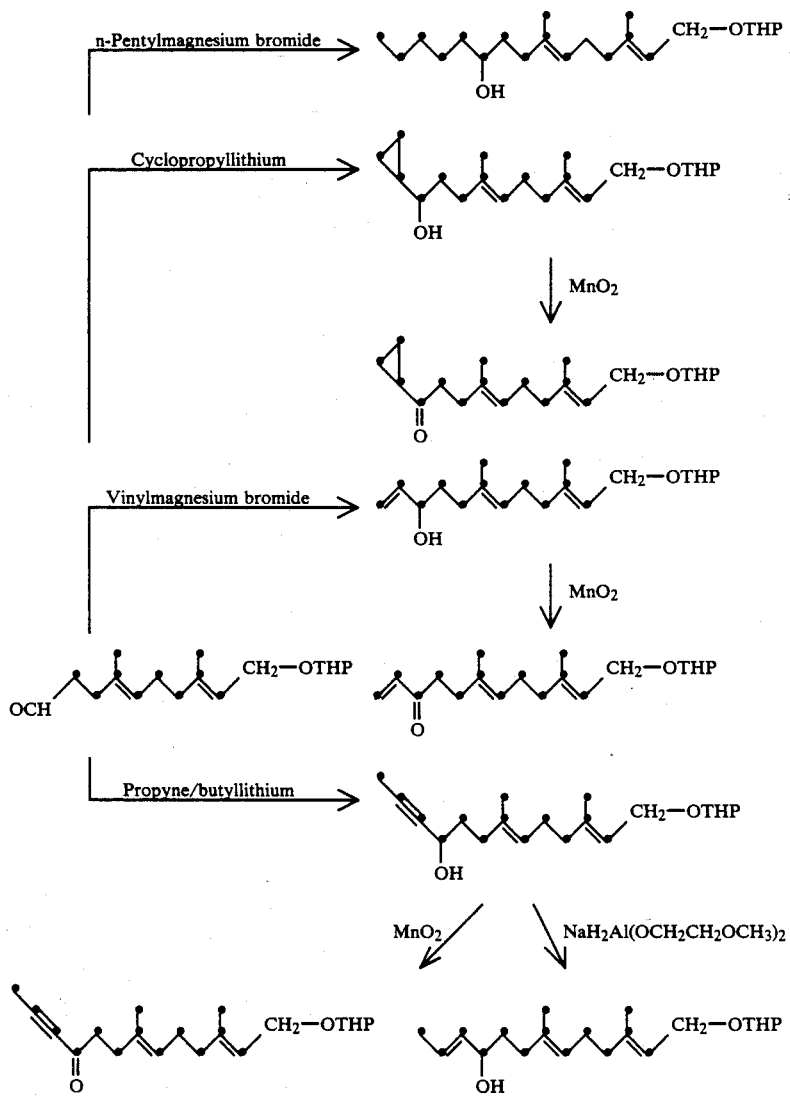

Scheme 4

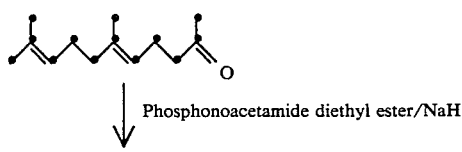

Phosphonoacetamide diethyl ester/NaH

Scheme 5

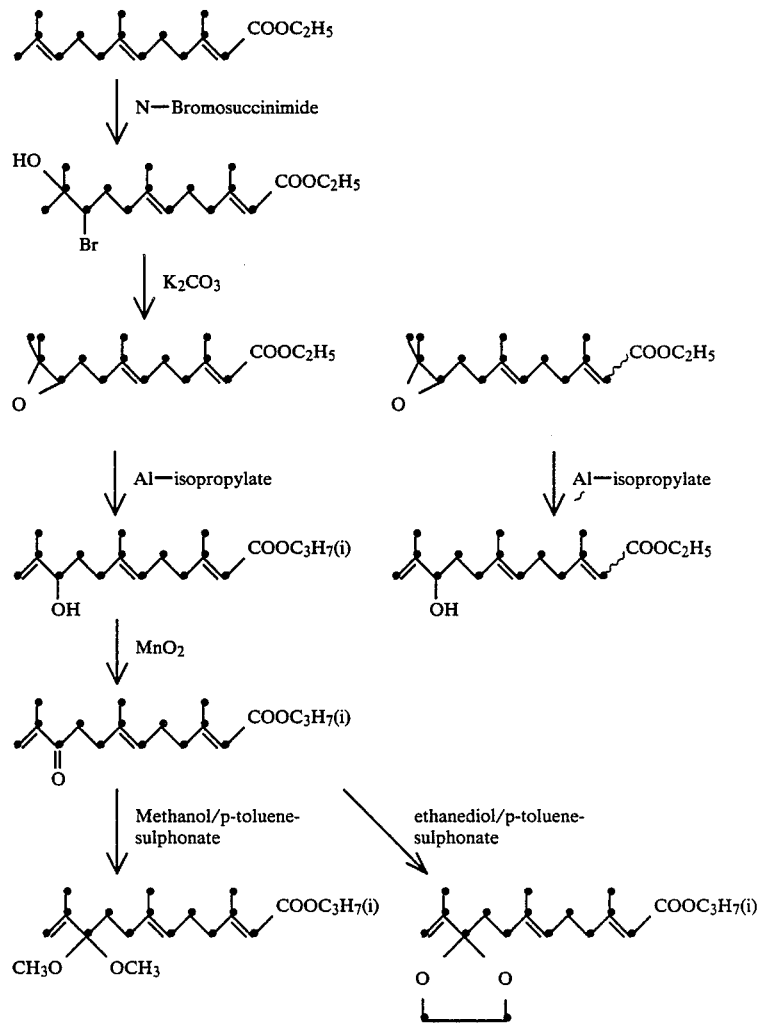

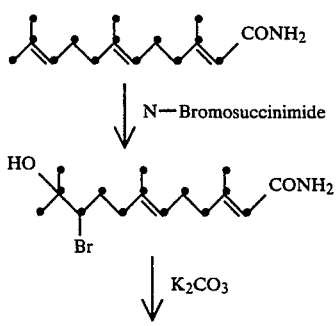

Furthermore, a number of the following Examples contain detailed information concerning the preparation of specific compounds which fall under one of formulae II to V.

The starting materials of formulae VI and VII as well as protected derivatives of compounds of formula VII are known or can be prepared readily according to methods which are known per se and which are familiar to any person skilled in the art.

As mentioned earlier, the compounds of general formula I as well as pharmaceutically usable salts of acidic compounds of formula I with bases have valuable pharmacodynamic properties.

Representative compounds of formula I were investigated with respect to their mucosa-protective and gastric acid secretion-inhibiting properties as well as to their toxicity.

The experimental procedure described hereinafter was used to determine the muscosa-protective property:

The oral administration of absolute ethanol to male rats in a dosage of 1 ml per rat leads within 1 hour to bloody lesions of the mucous membrane of the stomach. Various dosages of the substances to be tested (suspended in 0.125% carboxymethylcellulose) or of the vehicle alone (control) are administered to the rats orally (1 ml per rat) 30 minutes prior to the treatment with ethanol. One hour after the administration of the ethanol the animals are killed, their stomachs are investigated for the presence of lesions and the number and the total dimension of such lesions are determined. The $ID_{50}$ is that dosage of a test substance which reduces by 50% the number of lesions in comparison to the control group.

The test procedure described hereinafter was used to determine the gastric acid secretion-inhibiting activity:

The pylorus of male rats is ligated under slight ether narcosis in accordance with Shay et al. [Gastroenterology 5, 43 (1945)]. The substances to be tested, suspended in 0.5% carboxymethylcellulose, are administered intraduodenally. Control animals are treated only with the vehicle. Five hours after the ligation the animals are killed, the volume and acidity of their gastric juice are determined and the values obtained are compared with those of control animals. The $ID_{50}$ is that dosage of a test substance which brings about a 50% decrease of the secretion in comparison to the control animals.

In the following Table there are given for a series of representative compounds of formula I the results of the testing with respect to their mucosa-protective activity ("ethanol test") and to their gastric acid secretion-inhibiting activity. Moreover, this Table contains data concerning the acute toxicity ($LD_{50}$ in the case of single oral administration to mice).

| Compound | Ethanol Test ID 50 mg/kg p.o. | Gastric acid secretion-inhibition, ID 50 mg/kg | Toxicity LD 50 mg/kg p.o. |
| --- | --- | --- | --- |
| A | 0.55 | 2.0 | 1000–2000 |
| B | 0.62 | 68.2 | — |
| C | 0.78 | 80.3 | 1000–2000 |
| D | 0.79 | 66.0 | 1000–2000 |
| E | 0.93 | 18.4 | — |
| F | 1.30 | 27.7 | 625–1250 |
| G | 1.80 | 62.4 | 1000–2000 |
| H | 1.80 | 57.7 | 2500–5000 |
| I | 2.70 | 13.2 | >4000 |
| J | 3.40 | 63.9 | 1000–2000 |
| K | 3.60 | 60.8 | — |
| L | 4.40 | 73.4 | 625–1250 |
| M | 4.50 | 62.7 | 2500–5000 |
| N | 3.20 | 41.6 | >2000 |
| O | 26.8 | 48.8 | 1250–2500 |
| P | 5.0 | 79.6 | 1250–2500 |
| Q | 5.30 | 4.7 | >5000 |
| R | 6.40 | 28.6 | >5000 |
| S | 6.50 | 46.9 | — |
| T | 7.80 | 9.3 | — |
| U | 7.90 | 43.9 | 1000–2000 |
| V | 9.30 | 57.4 | — |

A = (all-E)-12-Hydroxy-6,10-dimethyl-6,10-dodecandien-1-yn-3-one
B = (all-E)-12-Hydroxy-6,10-dimethyl-1,6,10-dodecatrien-3-one
C = (all-E)-13-Hydroxy-7,11-dimethyl-7,11-tridecadien-2-yn-4-one
D = (all-E)-13-Hydroxy-7,11-dimethyl-2,7,11-tridecatrien-4-one
E = (all-E)-10,10-Diethoxy-3,7-dimethyl-2,6-dodecadien-11-yn-1-ol
F = (all-E)-12-Hydroxy-2,6,10-trimethyl-1,6,10-dodecatrien-3-one
G = (all-E)-10-Oxo-3,7,11-trimethyl-2,6,11-dodecatrienal
H = (6Z,10Z)-12-Hydroxy-2,6,10-trimethyl-1,6,10-dodecatrien-3-one
I = (all-E)-3,7-Dimethyl-9-[2-(1-methylvinyl)-1,3-dioxolan-2-yl]-2,6-nonadien-1-ol
J = (E,E)-3,7,11-Trimethyl-10-oxo-2,6,11-dodecatrienamide
K = (all-E)-13-Hydroxy-2,7,11-trimethyl-2,7,11-tridecatrien-4-one
L = (6E,10Z)-12-Hydroxy-2,6,10-trimethyl-1,6,10-dodecatrien-3-one
M = (6Z,10E)-12-Hydroxy-2,6,10-trimethyl-1,6,10-dodecatrien-3-one
N = (all-E)-3,7,11-trimethyl-2,6,11-dodecatriene-1,10-diol
O = (all-E)-10-Hydroxy-3,7,11-trimethyl-2,6,11-dodecatrienoic acid
P = (all-E)-10-Oxo-3,7,11-trimethyl-2,6,11-dodecatrienoic acid
Q = (all-E)-10,10-Dimethoxy-3,7,11-trimethyl-2,6,11-dodecatrien-1-ol
R = (all-E)-10-Hydroxy-3,7,11-trimethyl-2,6,11-dodecatrienal
S = (all-E)-12-Hydroxy-6,10-dimethyl-1-(trimethylsilyl)-6,10-dodecadien-1-yn-3-one
T = (2E,6E)-3,7,11-Trimethyl-10-oxo-2,6,11-dodecatrienal (E/Z)-oxime
U = (6E,10E)-12-Hydroxy-6,10-dimethyl-6,10-dodecadien-1-yn-3-one (E/Z)-O—methyl oxime
V = (2E,6E,11(E/Z))-3,7-Dimethyl-2,6,11-tridecatriene-1,10-diol The compounds and salts defined earlier can be used as medicaments, e.g. in the form of pharmaceutical preparations. Oral administration in the form of solid pharmaceutical preparations such as tablets, coated tablets, dragees, hard gelatine capsules and soft gelatine capsules primarily comes into consideration. Oral administration in the form of liquid pharmaceutical preparations such as solutions, emulsions and suspensions, rectal administration, e.g. in the form of suppositories, or parenteral administration, e.g. in the form of injection solutions, are of less consideration, but are not to be excluded.

Medicaments containing one of the compounds and salts defined earlier are likewise an object of the present invention. The manufacture of such medicaments can be effected by bringing one or more of the compounds and salts defined earlier and, if desired, one or more other therapeutically active substances into a galenical administration form together with one or more therapeutically inert excipients.

For the manufacture of tablets, coated tablets, dragees and hard gelatine capsules the compounds and salts defined earlier can be processed with pharmaceutically inert inorganic or organic excipients. As such excipients there can be used e.g. for tablets, dragees and hard gelatine capsules lactose, maize starch or derivatives thereof, talc, stearic acid or its salts etc. For the manufacture of pharmaceutical preparations which are resistant to gastric juice it is necessary to apply a gastric juice-resistant coating which can consist e.g. of hydroxypropylmethylcellulose phthlate.

For soft gelatine capsules there are suitable as excipients e.g. vegetable oils, waxes, fats, semi-solid and liquid polyols etc.

For the manufacture of solutions and syrups there are suitable as excipients e.g. water, polyols, saccharose, invert sugar, glucose and the like.

For suppositories there are suitable as excipients e.g. natural or hardened oils, waxes, fats, semi-liquid or liquid polyols and the like.

For injection solutions there are suitable as excipients e.g. water, alcohols, polyols, glycerine, vegetable oils etc.

The pharmaceutical preparations can contain, in addition, preserving agents, solubilizers, stabilizing agents, wetting agents, emulsifying agents, sweetening agents, colouring agents, flavoring agents, salts for varying the osmotic pressure, buffers, coating agents or antioxidants. They can also contain still other therapeutically valuable substances.

In accordance with the invention the compounds and salts defined earlier can be used in the control or prevention of illnesses, for example in the control or prevention of gastric ulcers and duodenal ulcers. The dosage can vary within wide limits and, of course, will be fitted to the individual requirements in each particular case. In general, in the case of oral administration a daily dosage of about 30–400 mg should be appropriate and in the case of intravenous administration a daily dosage of about 1–50 mg should be appropriate.

The use of the compounds and salts defined earlier for the manufacture of medicaments for the control or prevention of gastric ulcers and duodenal ulcers is also an object of the invention.

In the following Examples, which illustrate the present invention but which are not intended to limit its extent in any manner, all temperatures are given in degrees Celsius.

EXAMPLE 1

(a) A solution of 1 g (0.0038 mol) of ethyl (2Z,6E)-3,7,11-trimethyl-2,6,10-dodecatrienoate in 8 ml of toluene is treated dropwise at −5° to −10° with 9.45 ml of a solution of diisobutylaluminium hydride in toluene (1.2 mol/l). The solution is stirred at the same temperature for 1 hour under argon. The reaction mixture is poured into an ice-water mixture and extracted with ether. After drying and removing the solvent the residue is chromatographed on silica gel with ether-hexane 1:1. There is obtained (2Z,6E)-3,7,11-trimethyl-2,6,10-dodecatrien-1-ol which has the following bands in the IR spectrum; 3326 cm$^{-1}$, 1669 cm$^{-1}$, 1446 cm$^{-1}$, 1378 cm$^{-1}$, 1000 cm$^{-1}$.

A solution of 1 g (0.0045 mol) (2Z,6E)-3,7,11-trimethyl-2,6,11-dodecatrien-1-ol in 32 ml of 3,4-dihydro-2H-pyran is treated at 0° with 91 mg of p-toluenesulfonic acid. The solution is stirred at the same temperature for 2 hours under argon. After the addition of 100 ml of water the mixture is extracted with ether. The organic phase is washed with sodium bicarbonate solution. After drying and removing the solvent the residue is chromatographed on silica gel with ether-hexane 1:1. There is obtained tetrahydro-2-[[(2Z,6E)-3,7,11-trimethyl-2,6,10-dodecatrienyl]oxy]-2H-pyran which has the following bands in the IR spectrum: 1666 cm$^{-1}$, 1444 cm$^{-1}$, 1379 cm$^{-1}$, 1116 cm$^{-1}$, 1075 cm$^{-1}$, 1020 cm$^{-1}$.

(b) A solution of 2 g (0.0065 mol) of tetrahydro-2-[[(2Z,6E)-3,7,11-trimethyl-2,6,10-dodecatrienyl]oxy]-2H-pyran dissolved in 13 ml of monoglyme and 2.6 ml of water is treated portionwise at −10° with 1.3 g of N-bromosuccinimide. The mixture is subsequently stirred at 0° for ¼ hour and at room temperature for 2 hours. The reaction solution is poured into 100 ml of water and extracted with ethyl acetate. The organic phase is washed with saturated sodium chloride solution. After drying and removing the solvent the residue, containing tetrahydro-2-[[(2Z,6E)-10-bromo-11-hydroxy-3,7,11-trimethyl-2,6,10-dodecatrienyl]oxy]-2H-pyran, is dissolved in 18 ml of methanol and treated with 600 mg of potassium carbonate. The suspension is stirred at room temperature for 1.5 hours under argon. After removing the methanol on a rotary evaporator the residue is treated 500 ml of ether and 200 ml of water. The organic phase is washed with saturated sodium chloride solution. After drying and removing the solvent the residue, containing (6E,10Z)-2,3-epoxy-2,6,10-trimethyl-12-[(tetrahydro-2H-pyran-2-yl)oxy]-6,10-dodecadiene, is dissolved in 30 ml of toluene and treated with 1.35 g of aluminum isopropylate. The reaction mixture is boiled at reflux for 17 hours and, after cooling to room temperature, poured into 200 ml of an ice-water mixture. After acidification with 1N hydrochloric acid the mixture is extracted with 3×150 ml of hexane. The organic phase is washed with 500 ml of saturated sodium chloride solution. After drying and removing the solvent the residue is chromatographed on silica gel with a 1:2 ether-hexane mixture which additionally contains 0.1% triethylamine. There is obtained (6E,10Z)-2,6,10-trimethyl-12-[(tetrahydro-2H-pyran-2-yl)oxy]-1,6,10-dodecatrien-3-ol which has the following bands in the IR spectrum: 3445 cm$^{-1}$, 1648 cm$^{-1}$, 1441 cm$^{-1}$, 1375 cm$^{-1}$, 901 cm$^{-1}$.

(c) A solution of 0.5 g (0.0016 mol) of (6E,10Z)-2,6,10-trimethyl-12-[(tetrahydro-2H-pyran-2-yl)oxy]-1,6,10-dodecatrien-3-ol dissolved in 14.5 ml of tetrahydrofuran and 3.7 ml of water is treated with 167.2 mg (0.4 mol equivalents) of pyridinium p-toluenesulfonate. The solution is boiled at reflux for 17 hours. After cooling 100 ml of water and 300 ml of ether are added thereto. The organic phase is neutralized with sodium bicarbonate solution. After drying and removing the solvent the residue is chromatographed on silica gel with ether-hexane 1:1. There is obtained (6E,10Z)-2,6,10-trimethyl-1,6,10-dodecatriene-3,12-diol which has the following bands in the IR spectrum: 3344 cm$^{-1}$, 1647 cm$^{-1}$, 1449 cm$^{-1}$, 1375 cm$^{-1}$, 997 cm$^{-1}$.

EXAMPLE 2

A solution of 0.5 g (0.0016 mol) of (6E,10Z)-2,6,10-trimethyl-12-[(tetrahydro-2H-pyran-2-yl)oxy]-1,6,10-dodecatrien-3-ol dissolved in 15 ml of methylene chloride is treated with 10 g of manganese dioxide. The suspension is stirred at room temperature for 18 hours under argon. After filtration and removal of the solvent the residue is chromatographed on silica gel with ether-hexane 10:1. The product, containing (6E,10Z)-2,6,10-trimethyl-12-[(tetrahydro-2H-pyran-2-yl)oxy]-1,6,10-dodecatrien-3-one, is dissolved in 10 ml of tetrahydrofuran and 2.6 ml of water and treated with 118 mg of pyridinium p-toluenesulfonate. The solution is boiled at reflux for 17 hours. After cooling 100 ml of water and 200 ml of ether are added thereto. The organic phase is neutralized with sodium bicarbonate solution. After drying and removing the solvent the residue is chromatographed on silica gel with ether-hexane 1:1. There is obtained (6E,10Z)-12-hydroxy-2,6,10-trimethyl-1,6,10-dodecatrien-3-one which exhibits the following absorption bands in the IR spectrum: 3390 cm$^{-1}$, 1678 cm$^{-1}$, 1625 cm$^{-1}$, 1415 cm$^{-1}$, 1380 cm$^{-1}$, 945 cm$^{-1}$.

EXAMPLE 3

A solution of 0.5 g (0.0021 mol) of (6E,10Z)-12-hydroxy-2,6,10-trimethyl-1,6,10-dodecatrien-3-one dissolved in 5 ml of methylene chloride and 1.3 ml of pyridine is treated with 1 ml of acetic anhydride. The solution is stirred at room temperature for 18 hours under argon. After removing the solvent the residue is taken up three times in toluene and freed from the solvent on a rotary evaporator. The residue is chromatographed on silica gel with ether-hexane 1:5. There is obtained (2Z,6E)-3,7,11-trimethyl-10-oxo-2,6,11- dodecatrienyl acetate which has the following bands in the IR spectrum: 1735 cm$^{-1}$, 1677 cm$^{-1}$, 1630 cm$^{-1}$, 1448 cm$^{-1}$, 1368 cm$^{-1}$, 950 cm$^{-1}$.

EXAMPLE 4

(a) A solution of 1 g (0.0038 mol) of ethyl (2E,6Z)-3,7,11-trimethyl-2,6,10-dodecatrienoate in 8 ml of toluene is treated dropwise at −5° to −10° with 9.45 ml of a solution of diisobutylaluminium hydride in toluene (1.2 mol/l, i.e. 3.0 mol equivalents). The solution is stirred at the same temperature for 1 hour under argon. The reaction mixture is poured into an ice-water mixture and extracted with ether. After drying and removing the solvent the residue is chromatographed on silica gel with ether-hexane 1:1. There is obtained (2E,6Z)-3,7,11-trimethyl-2,6,10-dodecatrien-1-ol which has the following bands in the IR spectrum: 3323 cm$^{-1}$, 1668 cm$^{-1}$, 1446 cm$^{-1}$, 1377 cm$^{-1}$, 1001 cm$^{-1}$.

A solution of 1 g (0.0045 mol) of (2E,6Z)-3,7,11-trimethyl-2,6,10-dodecatrien-1-ol in 32 ml of 3,4-dihydro-2H-pyran is treated at 0° with 91 mg of p-toluenesulfonic acid. The solution is stirred at the same temperature for 2 hours under argon. After the addition of 100 ml of water the mixture is extracted with ether. The organic phase is washed with sodium carbonate solution. After drying and removing the solvent the residue is chromatographed on silica gel with ether-hexane 1:1. There is obtained tetrahyro-2-[[(2E,6Z)-3,7,11-trimethyl-2,6,10-dodecatrienyl]oxy]-2H-pyran which has the following bands in the IR spectrum: 1669 cm$^{-1}$, 1448 cm$^{-1}$, 1377 cm$^{-1}$, 1115 cm$^{-1}$, 1078 cm$^{-1}$, 1019 cm$^{-1}$.

A solution of 2 g (0.0065 mol) of tetrahydro-2-[[(2E,6Z)-3,7,11-trimethyl-2,6,10-dodecatrienyl]oxy]-2H-pyran dissolved in 13 ml of monoglyme and 2.6 ml of water is treated portionwise at −10° with 1.3 g of N-bromosuccinimide. The mixture is subsequently stirred at 0° for ¼ hour and at room temperature for 2 hours. The reaction solution is poured into 100 ml of water and extracted with ethyl acetate. The organic phase is washed with saturated sodium chloride solution. After drying and removing the solvent the residue, containing tetrahydro-2-[[(2E,6Z)-10-bromo-11-hydroxy-3,7,11-trimethyl-2,6,10-dodecatrienyl]oxy]-2H-pyran, is dissolved in 18 ml of methanol and treated with 600 mg of potassium carbonate. The suspension is stirred at room temperature for 1.5 hours under argon. After removing the methanol on a rotary evaporator the residue is treated with 500 ml of ether and 200 ml of water. The organic phase is washed with saturated sodium chloride solution. After drying and removing the solvent the residue, containing (6Z,10E)-2,3-epoxy-2,6,10-trimethyl-12-[(tetrahydro-2H-pyran-2-yl)-oxy]-6,10-dodecadiene, is dissolved in 30 ml of toluene and treated with 1.35 g of aluminum isopropylate. The reaction mixture is boiled at reflux for 17 hours. After cooling to room temperature the reaction mixture is poured into 200 ml of an ice-water mixture. After acidification with 1N hydrochloric acid the mixture is extracted with 3×150 ml of hexane. The organic phase is washed with 500 ml of saturated sodium chloride solution. After drying and removing the solvent the residue is chromatographed on silica gel with a 1:2 ether-hexane mixture which additionally contains 0.1% triethylamine. There is obtained (6Z,10E)-2,6,10-trimethyl-12-[(tetrahydro-2H-pyran-2-yl)oxy]-1,6,10-dodecatrien-3-ol which has the following bands in the IR spectrum: 3447 cm$^{-1}$, 1644 cm$^{-1}$, 1443 cm$^{-1}$, 1379 cm$^{-1}$, 909 cm$^{-1}$.

(b) A solution of 0.5 g (0.0016 mol) of (6Z,10E)-2,6,10-trimethyl-12-[(tetrahydro-H-pyran-2-yl)oxy]-1,6,10-dodecatrien-3-ol dissolved in 14.5 ml of tetrahydrofuran and 3.7 ml of water is treated with 167.2 mg (0.4 mol equivalents) of pyridinium p-toluenesulfonate. The solution is boiled at reflux for 17 hours. After cooling 100 ml of water and 300 ml of ether are added. The organic phase is neutralized with sodium bicarbonate solution. After drying and removing the solvent the residue is chromatographed on silica gel with ether-hexane 1:1. There is obtained (6E,10Z)-2,6,10-trimethyl-1,6,10-dodecatriene-3,12-diol which has the following bands in the IR spectrum: 3346 cm$^{-1}$, 1649 cm$^{-1}$, 1446 cm$^{-1}$, 1377 cm$^{-1}$, 1001 cm$^{-1}$.

EXAMPLE 5

A solution of 0.5 g (0.0016 mol) of (6Z,10E)-2,6,10-trimethyl-12-[(tetrahydro-2H-pyran-2-yl)oxy]-1,6,10-dodecatrien-3-ol dissolved in 15 ml of methylene chloride is treated with 10 g of manganese dioxide. The suspension is stirred at room temperature for 18 hours under argon. After filtration and removal of the solvent the residue is chromatographed on silica gel with ether-hexane 10:1. The product, containing (6Z,10E)-2,6,10-trimethyl-12-[(tetrahydro-2H-pyran-2-yl)oxy]-1,6,10-dodecatrien-3-one, is dissolved in 10 ml of tetrahydrofuran and 2.6 ml of water and treated with 118 mg of pyridinium p-toluenesulfonate. The solution is boiled at reflux for 17 hours. After cooling 100 ml of water and 200 ml of ether are added thereto. The organic phase is neutralized with sodium bicarbonate solution. After drying and removing the solvent the residue is chromatographed on silica gel with ether-hexane 1:1. There is obtained (6Z,10E)-12-hydroxy-2,6,10-trimethyl-1,6,10-dodecatrien-3-one which exhibits the following absorption bands in the IR spectrum: 3389 cm$^{-1}$, 1675 cm$^{-1}$, 1626 cm$^{-1}$, 1413 cm$^{-1}$, 1382 cm$^{-1}$, 1000 cm$^{-1}$, 948 cm$^{-1}$.

EXAMPLE 6

A solution of 0.5 g (0.0021 mol) of (6Z,10E)-12-hydroxy-2,6,10-trimethyl-1,6,10-dodecatrien-3-one dissolved in 5 ml of methylene chloride and 1.3 ml of pyridine is treated with 1 ml of acetic anhydride. The solution is stirred at room temperature for 18 hours under argon. After removing the solvent the residue is taken up three times in toluene and freed from solvent on a rotary evaporator. The residue is chromatographed on silica gel with ether-hexane 1:5. There is obtained (2E,6Z)-3,7,11-trimethyl-10-oxo-2,6,11-dodecatrienyl acetate which has the following bands in the IR spectrum: 1739 cm$^{-1}$, 1675 cm$^{-1}$, 1629 cm$^{-1}$, 1449 cm$^{-1}$, 1370 cm$^{-1}$, 948 cm$^{-1}$.

EXAMPLE 7

(a) A solution of 1 g (0.0038 mol) of ethyl (2Z,6Z)-3,7,11-trimethyl-2,6,10-dodecatrienoate in 8 ml of toluene is treated dropwise at −5° to −10° with 9.45 ml of a solution of diisobutylaluminium hydride in toluene (1.2 mol/l, i.e. 3.0 mol equivalents). The solution is stirred at the same temperature for 1 hour under argon. The reaction mixture is poured into an ice-water mixture and extracted with ether. After drying and removing the solvent the residue is chromatographed on silica gel with ether-hexane 1:1. There is obtained (2Z,6Z)-3,7,11-trimethyl-2,6,10-dodecatrien-1-ol which has the following bands in the IR spectrum: 3327 cm$^{-1}$, 1666 cm$^{-1}$, 1448 cm$^{-1}$, 1379 cm$^{-1}$, 999 cm$^{-1}$.

A solution of 1 g (0.0045 mol) of (2Z,6Z)-3,7,11-trimethyl-2,6,10-dodecatrien-1-ol in 32 ml of 3,4-dihydro-2H-pyran is treated at 0° with 91 mg of p-toluenesulfonic acid. The solution is stirred at the same temperature for 2 hours under argon. After the addition of 100 ml of water the mixture is extracted with ether. The organic phase is washed with sodium bicarbonate solution. After drying and removing the solvent the residue is chromatographed on silica gel with ether-hexane 1:1. There is obtained tetrahydro-2-[[(2Z,6Z)-3,7,11-trimethyl-2,6,10-dodecatrienyl]oxy]-2H-pyran which has the following bands in the IR spectrum: 1668 cm$^{-1}$, 1444 cm$^{-1}$, 1378 cm$^{-1}$, 1118 cm$^{-1}$, 1075 cm$^{-1}$, 1023 cm$^{-1}$.

A solution of 2 g (0.0065 mol) of tetrahydro-2-[[(2Z,6Z)-3,7,11-trimethyl-2,6,10-dodecatrienyl]oxy]-2H-pyran dissolved in 13 ml of monoglyme and 2.6 ml of water is treated portionwise at −10° with 1.3 g of N-bromosuccinimide. The mixture is subsequently stirred at 0° for ¼ hour and at room temperature for 2 hours. The reaction solution is poured into 100 ml of water and extracted with ethyl acetate. The organic phase is washed with saturated sodium chloride solution. After drying and removing the solvent the residue, containing tetrahydro-2-[[(2Z,6Z)-10-bromo-11-hydroxy-3,7,11-trimethyl-2,6,10-dodecatrienyl]oxy]-2H-pyran, is dissolved in 18 ml of methanol and treated with 600 mg of potassium carbonate. The suspension is stirred at room temperature for 1.5 hours under argon. After removing the methanol on a rotary evaporator the residue is treated with 500 ml of ether and 200 ml of water. The organic phase is washed with saturated sodium chloride solution. After drying and removing the solvent the residue, containing (6Z,10Z)-2,3-epoxy-2,6,10-trimethyl-12-[(tetrahydro-2H-pyran-2-yl)oxy]-6,10-dodecadiene, is dissolved in 30 ml of toluene and treated with 1.35 g of aluminum isopropylate. The reaction mixture is boiled at reflux for 17 hours. After cooling to room temperature the reaction mixture is poured into 200 ml of an ice-water mixture. After acidification with 1N hydrochloric acid the mixture is extracted with 3×150 ml of hexane. The organic phase is washed with 500 ml of saturated sodium chloride solution. After drying and removing the solvent the residue is chromatographed on silica gel with a 1:2 ether-hexane mixture which additionally contains 0.1% triethylamine. There is obtained (6Z,10Z)-2,6,10-trimethyl-12-[(tetrahydro-2H-pyran-2-yl)oxy]-1,6,10-dodecatrien-3-ol which has the following bands in the IR spectrum: 3449 cm$^{-1}$, 1647 cm$^{-1}$, 1449 cm$^{-1}$, 1377 cm$^{-1}$, 901 cm$^{-1}$.

(b) A solution of 0.5 g (0.0016 mol) of (6Z,10Z)-2,6,10-trimethyl-12-[(tetrahydro-2H-pyran-2-yl)oxy]-1,6,10-dodecatrien-3-ol dissolved in 14.5 ml of tetrahydrofuran and 3.7 ml of water is treated with 167.2 mg (0.4 mol equivalents) of pyridinium p-toluenesulfonate. The solution is boiled at reflux for 17 hours. After cooling 100 ml of water and 300 ml of ether are added thereto. The organic phase is neutralized with sodium bicarbonate solution. After drying and removing the solvent the residue is chromatographed on silica gel with ether-hexane 1:1. There is obtained (6Z,10Z)-1,6,10-dodecatriene-3,12-diol which has the following bands in the IR spectrum: 3448 cm$^{-1}$, 1646 cm$^{-1}$, 1443 cm$^{-1}$, 1375 cm$^{-1}$, 998 cm$^{-1}$.

EXAMPLE 8

A solution of 0.5 g (0.0016 mol) of (6Z,10Z)-2,6,10-trimethyl-12-[(tetrahydro-2H-pyran-2-yl)oxy]-1,6,10-dodecatrien-3-ol dissolved in 15 ml of ethylene chloride is treated with 10 g of manganese dioxide. The suspension is stirred at room temperature for 18 hours under argon. After filtration and removal of the solvent the residue is chromatographed on silica gel with ether-hexane 10:1. The product, containing (6Z,10Z)-2,6,10-trimethyl-12-[(tetrahydro-2H-pyran-2-yl)oxy]-1,6,10-dodecatrien-3-one, is dissolved in 10 ml of tetrahydrofuran and 2.6 ml of water and treated with 118 mg of pyridinium p-toluenesulfonate. The solution is boiled at reflux for 17 hours. After cooling 100 ml of water and 200 ml of ether are added thereto. The organic phase is neutralized with sodium bicarbonate solution. After drying and removing the solvent the residue is chromatographed on silica gel with ether-hexane 1:1. There is obtained (6Z,10Z)-12-hydroxy-2,6,10-trimethyl-1,6,10-dodecatrien-3-one which exhibits the following absorption bands in the IR spectrum: 3387 cm$^{-1}$, 1677 cm$^{-1}$, 1629 cm$^{-1}$, 1417 cm$^{-1}$, 1389 cm$^{-1}$, 997 cm$^{-1}$, 950 cm$^{-1}$.

EXAMPLE 9

A solution of 0.5 g (0.0021 mol) of (6Z,10Z)-12-hydroxy-2,6,10-trimethyl-1,6,10-dodecatrien-3-one dissolved in 5 ml of methylene chloride and 1.3 ml of pyridine is treated with 1 ml of acetic anhydride. The solution is stirred at room temperature for 18 hours under argon. After removing the solvent the residue is taken up three times in toluene and freed from solvent each time on a rotary evaporator. The residue is chromatographed on silica gel with ether-hexane 1:5. There is obtained (2Z,6Z)-3,7,11-trimethyl-10-oxo-2,6,11-dodecatrienyl acetate which has the following bands in the IR spectrum: 1742 cm$^{-1}$, 1671 cm$^{-1}$, 1634 cm$^{-1}$, 1442 cm$^{-1}$, 1367 cm$^{-1}$, 951 cm$^{-1}$.

EXAMPLE 10

(a) A solution of 2.0 g of (6E,10Z)-2,6,10-trimethyl-12-[(tetrahydro-2H-pyran-2-yl)oxy]-1,6,10-dodecatrien-3-ol and 4.23 g of imidazole in 30 ml of dimethylformamide is treated with 4.7 g (5 mol equivalents) of tert.-butyl-dimethylchlorosilane. The reaction mixture is stirred at room temperature for 6 hours under argon. After aqueous working-up the organic phase is dried and freed from the solvents. The residue is chromatographed on silica gel with ether-hexane 1:10.

The product, containing (6E,10Z)-3-(tert.-butyldimethylsilyloxy)-2,6,10-trimethyl-12-[(tetrahydro-2H-pyran-2-yl)oxy]-1,6,10-dodecatriene, is dissolved in 50 ml of isopropanol and treated with 350 mg of pyridinium p-toluenesulfonate. The reaction solution is stirred at room temperature for 6 hours under argon. After aqueous working-up the organic phase is dried and freed from the solvents. The residue is chromatographed on silica gel with ether-hexane 2:1. There is obtained (2Z,6E)-10-(tert.butyldimethylsilyloxy)-3,7,11-trimethyl-2,6,11-dodecatrien-1-ol which exhibits the following absorption bands in the IR spectrum: 3339 cm$^{-1}$, 3071 cm$^{-1}$, 1666 cm$^{-1}$, 1651 cm$^{-1}$, 1448 cm$^{-1}$, 1251 cm$^{-1}$, 1078 cm$^{-1}$, 1022 cm$^{-1}$, 1004 cm$^{-1}$.

(b) A solution of 200 mg of (2Z,6E)-10-(tert.butyldimethylsilyloxy)-3,7,11-trimethyl-2,6,11-dodecatrien-1-ol in 5 ml of methylene chloride is treated with 0.4 ml of triethylamine and 0.2 ml of acetic anhydride. The solution is stirred at room temperature for 6 hours and subsequently freed from the solvents on a rotary evaporator. The residue is taken up three times in toluene and freed from volatile constituents each time on a rotary evaporator. The crude product is chromatographed on silica gel with ether-hexane 1:5.

The purified product obtained, (2Z,6E)-10-(tert.-butyldimethylsilyloxy)-3,7,11-trimethyl-2,6,11-dodecatrienyl acetate, is dissolved in 5 ml of tetrahydrofuran and treated with 320 mg of tetrabutylammonium fluoride. The solution is stirred at room temperature for 16 hours. After removing the solvent on a rotary evaporator the residue is chromatographed on silica gel with ether-hexane 1:1. There is obtained (2Z,6E)-10-hydroxy-3,7,11-trimethyl-2,6,11-dodecatrienyl acetate which exhibits the following bands in the IR spectrum: 3454 cm$^{-1}$, 1739 cm$^{-1}$, 1651 cm$^{-1}$, 1446 cm$^{-1}$, 1236 cm$^{-1}$, 1023 cm$^{-1}$, 955 cm$^{-1}$, 898 cm$^{-1}$.

EXAMPLE 11

A solution of 3.5 g (0.0148 mol) of (6E,10Z)-12-hydroxy-2,6,10-trimethyl-1,6,10-dodecatrien-3-one in 110 ml of methanol is treated with 7.15 g of N-(2-acetylthioethyl)acetamide and 6.2 ml of triethylamine. The solution is stirred under argon at room temperature for 24 hours. The solvents are removed on a rotary evaporator. The residue is taken up three times with toluene and freed from solvent on a rotary evaporator. The crude product can be used directly for the acetylation described in Example 12 or can be chromatographed on silica gel with ether-methanol 15:1. After chromatographic purification there is obtained (2Z,6E)-12-[(2-acetamidoethyl)thio]-3,7,11-trimethyl-10-oxo-2,6-dodecadien-1-ol which exhibits the following bands in the IR spectrum: 1737 cm$^{-1}$, 1715 cm$^{-1}$, 1437 cm$^{-1}$, 1366 cm$^{-1}$, 1277 cm$^{-1}$, 1235 cm$^{-1}$, 1157 cm$^{-1}$, 1136 cm$^{-1}$, 1022 cm$^{-1}$.

EXAMPLE 12

The crude (2Z,6E)-12-[(2-acetamidoethyl)thio]-3,7,11-trimethyl-10-oxo-2,6-dodecadien-1-ol obtained in accordance with Example 11 is dissolved at 0° in 160 ml of methylene chloride and treated with 32 ml of acetic anhydride and 42 ml of pyridine. The solution is stirred at room temperature for 20 hours under argon. The solvents are removed in a water-jet vacuum. The residue is taken up three times with toluene and freed from solvent each time on a rotary evaporator. The crude product is chromatographed on silica gel with ether-methanol. There is obtained (2Z,6E)-12-[(2-acetamidoethyl)thiol]-3,7,11-trimethyl-10-oxo-2,6-dodecadienyl acetate which has the following absorption bands in the IR spectrum: 1736 cm$^{-1}$, 1712 cm$^{-1}$, 1658 cm$^{-1}$, 1545 cm$^{-1}$, 1375 cm$^{-1}$, 1235 cm$^{-1}$, 1023 cm$^{-1}$, 992 cm$^{-1}$.

EXAMPLE 13

A solution of 300 mg (0.0013 mol) of (6E,10Z)-12-hydroxy-2,6,10-trimethyl-1,6,10-dodecatrien-3-one in 10 ml of methanol is treated with 0.27 ml of 2-mercaptoethanol and 0.53 ml of triethylamine. The solution is stirred at room temperature for 18 hours under argon. After removing the solvent on a rotary evaporator the residue is treated with water and methylene chloride. After extraction the organic phase is dried and freed from solvent on a rotary evaporator. The residue is chromatographed on silica gel with ether-methanol 50:1. There is obtained (6E,10Z)-12-hydroxy-1-[(2-hydroxyethyl)thio]-2,6,10-trimethyl-6,10-dodecadien-3-one which has the following absorption bands in the IR spectrum: 3369 cm$^{-1}$, 1708 cm$^{-1}$, 1667 cm$^{-1}$, 1450 cm$^{-1}$, 1044 cm$^{-1}$, 1055 cm$^{-1}$.

EXAMPLE 14

A solution of 300 mg (0.00096 mol) of (6E,10Z)-12-hydroxy-1-[2-hydroxyethyl)thio]-2,6,10-trimethyl-6,10-dodecadien-3-one in 10 ml of methylene chloride is treated with 1.1 ml of pyridine and 0.9 ml of acetic anhydride. The solution is stirred at room temperature for 18 hours under argon. After removing the solvents the residue is taken up three times in toluene and freed from solvent on a rotary evaporator. The residue is chromatographed on silica gel with ether. There is obtained (2Z,6E)-12-[(2-acetoxyethyl)thio]-3,7,11-trimethyl-2,6-dodecadienyl acetate which has the following absorption bands in the IR spectrum: 1740 cm$^{-1}$, 1712 cm$^{-1}$, 1450 cm$^{-1}$, 1379 cm$^{-1}$, 1235 cm$^{-1}$, 1025 cm$^{-1}$, 957 cm$^{-1}$.

EXAMPLE 15

A solution of 4 g (0.0017 mol) of (6E,10Z)-12-hydroxy-2,6,10-trimethyl-1,6,10-dodecatrien-3-one in 13 ml of methanol is treated with 4.7 ml of methyl thioglycolate and 7.1 ml of triethylamine. The solution is stirred at room temperature for 18 hours under argon. After removing the solvent the residue is worked-up with water and methylene chloride. The organic phase is dried and freed from solvent. The residue is chromatographed on silica gel with ether. There is obtained methyl [[(6E,10Z)-12-hydroxy-2,6,10-trimethyl-3-oxo-6,10-dodecadienyl]thio]acetate which has the following bands in the IR spectrum: 1736 cm$^{-1}$, 1711 cm$^{-1}$, 1437 cm$^{-1}$, 1408 cm$^{-1}$, 1281 cm$^{-1}$, 1137 cm$^{-1}$, 1007 cm$^{-1}$.

EXAMPLE 16

A solution of 300 mg (0.00088 mol) of methyl [[(6E,10Z)-12-hydroxy-2,6,10-trimethyl-3-oxo-6,10-dodecadienyl]thio]acetate in 5 ml of methylene chloride is treated with 0.5 ml of pyridine and 0.4 ml of acetic anhydride. The solution is stirred at room temperature for 18 hours under argon. After removing the solvent the residue is taken up three times in toluene and freed from solvent each time on a rotary evaporator. The residue is chromatographed on silica gel with ether. There is obtained (2Z,6E)-12-[[(methoxycarbonyl)methyl]thio]-3,7,11-trimethyl-10-oxo-2,6-dodecadienyl acetate which exhibits the following bands in the IR spectrum: 1710 cm$^{-1}$, 1657 cm$^{-1}$, 1552 cm$^{-1}$, 1445 cm$^{-1}$, 1375 cm$^{-1}$, 1290 cm$^{-1}$, 1235 cm$^{-1}$.

EXAMPLE 17

A solution of 4 g (0.017 mol) of (6Z,10E)-12-hydroxy-2,6,10-trimethyl-1,6,10-dodecatrien-3-one in 100 ml of methylene chloride is treated with 6 ml of thioacetic acid and 4.7 ml of triethylamine. The solution is stirred at room temperature for 21 hours under argon. After removing the solvent the residue is treated with water and methylene chloride. After extraction the organic phase is dried and freed from solvent. The residue is chromatographed on silica gel with ether. There is obtained S-[(6Z,10E)-12-hydroxy-2,6,10-trimethyl-3-oxo-6,10-dodecadienyl]thioacetate which has the following bands in the IR spectrum: 3414 cm$^{-1}$, 1694 cm$^{-1}$, 1454 cm$^{-1}$, 1135 cm$^{-1}$, 1107 cm$^{-1}$.

EXAMPLE 18

A solution of 3.5 g (0.0015 mol) of (6Z,10Z)-12-hydroxy-2,6,10-trimethyl-1,6,10-dodecatrien-3-one in 110 ml of methanol is treated with 9.7 g of S-[(2-acetamido-2-methoxycarbonyl)ethyl]thioacetate and 6.2 ml of triethylamine. The solution is stirred at room temperature for 24 hours. After removing the solvent the residue is taken up three times in toluene and freed from solvent each time on a rotary evaporator. The residue is chromatographed on silica gel with ether-methanol 50:1. There is obtained methyl N-acetyl-3-[[(6Z,10Z)-12-hydroxy-2,6,10-trimethyl-3-oxo-6,10-dodecadienyl]thio]alaninate which has the following bands in the IR spectrum: 3289 cm$^{-1}$, 1746 cm$^{-1}$, 1711 cm$^{-1}$, 1661 cm$^{-1}$, 1541 cm$^{-1}$, 1438 cm$^{-1}$, 1374 cm$^{-1}$, 1214 cm$^{-1}$.

EXAMPLE 19

A solution of 3.5 g of methyl N-acetyl-3-[[(6Z,10Z)-12-hydroxy-2,6,10-trimethyl-3-oxo-6,10-dodecadienyl]-thio]alaninate dissolved in 15 mil of methylene chloride is treated at 0° with 39 ml of pyridine and 30 ml of acetic anhydride. The solution is stirred at room temperature for 20 hours. After removing the solvent the residue is taken up three times in toluene and freed from solvent each time on a rotary evaporator. The crude product is chromatographed on silica gel with ether-methanol 50:1. There is obtained methyl N-acetyl-3-[[(6Z,10Z)-12-acetoxy-2,6,10-trimethyl-3-oxo-6,10-dodecadienyl]-thio]alaninate which exhibits the following absorption bands in the IR spectrum: 1738 cm$^{-1}$, 1713 cm$^{-1}$, 1664 cm$^{-1}$, 1438 cm$^{-1}$, 1412 cm$^{-1}$, 1236 cm$^{-1}$, 1117 cm$^{-1}$.

EXAMPLE 20

(a) A solution of 5 g of E-geranylacetone in 90 ml of dimethoxyethane is treated at −20° with 25.1 g of phosphonoacetamide diethyl ester and 1.86 g of 50% sodium hydride dispersion in mineral oil. The reaction mixture is stirred at room temperature for 3.5 hours under argon. After the addition of water the mixture is extracted with ethyl acetate. The organic phase is dried and freed from solvent. Crystallization of the (2E/Z,6E)-3,7,11-trimethyl-2,6,10-dodecatrienamide (4:1 2E/Z mixture), which remains behind as the residue, from hexane gives white crystals, m.p. 51°–52.5°. This material is recrystallized a further twice from hexane, there being obtained pure (E,E)-3,7,11-trimethyl-2,6,10-dodecatrienamide as a white crystalline material of m.p. 53°–53.5°.

(b) 8.0 g of N-bromosuccinimide are added portionwise at 0° within 20 minutes to a mixture of 9.4 g of (E,E)-3,7,11-trimethyl-2,6,10-dodecatrienamide in 80 ml of -1,2-dimethoxyethane. The reaction mixture is stirred at 0° for 1 hour and at room temperature for 2 hours and then poured into a mixture of 500 ml of saturated sodium chloride solution and ice, whereupon the mixture is extracted with 2×300 ml of ether. The combined extracts are washed with saturated sodium chloride solution and water, dried over sodium sulphate, filtered and concentrated. There is obtained crude (E,E)-10-bromo-11-hydroxy-3,7,11-trimethyl-2,6-dodecadienamide as a yellow oil.

This oil is dissolved in 50 ml of methanol, whereupon the solution is treated with 5.66 g of potassium carbonate and stirred at room temperature for 3 hours. After the addition of 500 ml of saturated sodium chloride solution the mixture is extracted with 2×300 ml of ether, whereupon the combined extracts are washed with saturated sodium chloride solution and water, dried over sodium sulphate, filtered and evaporated. The yellow oil obtained is chromatographed on 500 g of silica gel with hexane-ether (25% to 100%)/0.1% triethylamine as the elution agent. There is obtained (E,E)-10,11-epoxy-3,7,11-trimethyl-2,6-dodecadienamide as a yellowish oil. IR (film): 3398, 3338, 3192 (NH$_2$): 1672 (amide C=O). MS (CI with NH$_3$): 252 (M+H)$^+$.

(c) A solution of 4.8 g of (E,E)-10,11-epoxy-3,7,11-trimethyl-2,6-dodecadienamide in 70 ml of toluene is treated with 4.48 g of aluminum isopropylate, whereupon the mixture is boiled under reflux for 4.5 hours. The cooled reaction mixture is poured into a mixture of 2N hydrochloric acid and ice, whereupon the mixture is extracted with 2×100 ml of ether. The combined organic extracts are washed with water and with saturated sodium bicarbonate solution, dried over sodium sulphate, filtered and evaporated. The residue is chromatographed on 230 g of aluminum oxide (basic, activity III), elution being carried out with hexane-ethyl acetate (20% to 100%) and then with ethyl acetate-methanol (10%). There is obtained (E,E)-10-hydroxy-3,7,11-trimethyl-2,6,11-dodecatrienamide as a yellowish, viscous oil. IR (film): 3335, 3195 (OH and NH$_2$); 1668 (amide C=O). MS (CI with NH$_3$): 252 (M+H)$^+$; 251 (M+NH$_4$-H$_2$O)$^+$.

EXAMPLE 21

A solution of 1.9 g of (E,E)-10-hydroxy-3,7,11-trimethyl-2,6,11-dodecatrienamide in 50 ml of methylene chloride is treated with 19.0 g of manganese dioxide ("precipitated", activated by heating to 110° for 15 minutes) and the resulting suspension is stirred at room temperature for 16 hours. After filtration over Hyflo the filtrate is concentrated and the yellow oil obtained is chromatographed on 100 g of aluminum oxide (neutral, activity III) with hexane-ethyl acetate (50% to 100%). There is obtained (E,E)-3,7,11-trimethyl-10-oxo-2,6,11-dodecatrienamide as a colourless oil which crystallizes upon standing, m.p. 42°–44°. IR (film): 3428, 3347, 3194, (NH$_2$); 1671 (amide C=O, ketone conj. C=O). MS (CI with NH$_3$): 250 (M+H)$^+$.

EXAMPLE 22

A solution of 4.1 g (0.016 mol) of (E,E)-3,7,11-trimethyl-10-oxo-2,6,11-dodecatrienamide in 125 ml of methanol is treated with 3.5 ml of 2-mercaptoethanol and 7 ml of triethylamine. The solution is stirred at room temperature for 18 hours. After removing the solvent the residue is taken up three times in toluene and freed from solvent on a rotary evaporator. The residue is chromatographed on silica gel with ether-methanol 10:1. There is obtained (2E,6E)-12-(2-hydroxyethyl)-3,7,11-trimethyl-10-oxo-2,6-dodecadienamide which exhibits the following absorption bands in the IR spectrum: 3340 cm$^{-1}$, 3201 cm$^{-1}$, 2924 cm$^{-1}$, 1707 cm$^{-1}$, 1669 cm$^{-1}$, 1608 cm$^{-1}$, 1409 cm$^{-1}$, 1369 cm$^{-1}$, 1305 cm$^{-1}$, 1046 cm$^{-1}$, 1012 cm$^{-1}$.

EXAMPLE 23

A solution of 1.75 g of (2E,6E)-12-(2-hydroxyethyl)-3,7,11-trimethyl-10-oxo-2,6-dodecadienamide dissolved in 87 ml of methylene chloride is treated at 0° with 1.02 g of m-chloroperbenzoic acid. The solution is stirred at 0° for 1.5 hours under argon. The reaction solution is washed with aqueous potassium carbonate solution. After drying and removing the solvent the residue is chromatographed on silica gel with ether-methanol 1:1. There is obtained (2E,6E)-12-[(2-hydroxyethyl)sulfinyl]-3,7,11-trimethyl-10-oxo-2,6-dodecadienamide which exhibits the following bands in the IR spectrum: 3335 cm$^{-1}$, 3201 cm$^{-1}$, 1710 cm$^{-1}$, 1669 cm$^{-1}$, 1438 cm$^{-1}$, 1407 cm$^{-1}$, 1369 cm$^{-1}$, 1020 cm$^{-1}$, 995 cm$^{-1}$.

EXAMPLE 24

A solution of 2.0 g (0.008 mol) of (E,E)-3,7,11-trimethyl-10-oxo-2,6,11-dodecatrienamide in 60 ml of methanol is treated with 2.3 ml of methyl thioglycolate and 3.4 ml of triethylamine. The solution is stirred at room temperature for 8 hours under argon. After removing the solvent the residue is taken up in water and methylene chloride. After extraction the organic phase is dried and freed from solvent. The residue is chromatographed on silica gel with ether-methanol 20:1. There is obtained methyl [[(6E,10E)-11-carbamoyl-2,6,10-trimethyl-3-oxo-6,10-undecadienyl]thio]acetate which exhibits the following absorption bands in the IR spectrum: 3447 cm$^{-1}$, 3352 cm$^{-1}$, 3195 cm$^{-1}$, 1735 cm$^{-1}$, 1712 cm$^{-1}$, 1669 cm$^{-1}$, 1638 cm$^{-1}$ 1609 cm$^{-1}$, 1436 cm$^{-1}$, 1300 cm$^{-1}$, 1137 cm$^{-1}$, 1008 cm$^{-1}$.

EXAMPLE 25

A solution of 500 mg (0.0014 mol) of methyl [[(6E,10E)-11-carbamoyl-2,6,10-trimethyl-3-oxo-6,10-undecadienyl]thio]acetate in 30 ml of methylene chloride is treated at 0° with 270 mg of m-chloroperbenzoic acid. The solution is stirred at 0° for 1 hour under argon. The reaction solution is washed with aqueous potassium carbonate solution. After drying and removing the solvent the residue is chromatographed on silica gel with ether-methanol 3:1. There is obtained methyl [[(6E,10E)-11-carbamoyl-2,6,10-trimethyl-3-oxo-6,10-undecadienyl]sulfinyl]acetate which exhibits the following absorption bands in the IR spectrum: 3329 cm$^{-1}$, 3197 cm$^{-1}$, 1734 cm$^{-1}$, 1671 cm$^{-1}$, 1639 cm$^{-1}$, 1610 cm$^{-1}$, 1439 cm$^{-1}$, 1307 cm$^{-1}$, 1218 cm$^{-1}$, 1193 cm$^{-1}$, 1148 cm$^{-1}$, 1016 cm$^{-1}$.

EXAMPLE 26

(a) 43.6 g (0.155 mol) of ethyl (all-E)-10,11-epoxy-3,7,11-trimethyl-2,6-dodecadienoate are added dropwise at 110° to a mixture of 32 g (0.156 mol) of aluminum isopropylate and 300 ml of toluene. The reaction mixture is boiled under reflux for a further 12 hours and then poured into ice-water, whereupon the mixture is neutralized with 2N hydrochloric acid and extracted with hexane. The combined organic phases are firstly washed with saturated sodium chloride solution, then dried over sodium sulphate and evaporated. For purification, the residue is chromatographed on silica gel with hexane-ethyl acetate 4:1, there being obtained isopropyl (all-E)-10-hydroxy-3,7,11-trimethyl-2,6,11-dodecatrienoate. CI-MS (NH$_3$): 295 (M+H)$^+$, 277 (M+H—H$_2$O)$^+$, 235 (M+H—HO—<)$^+$.

(b) 4.8 g (0.016 mol) of isopropyl (all-E)-10-hydroxy-3,7,11-trimethyl-2,6,11-dodecatrienoate and 45 ml of 1N sodium hydroxide solution are boiled under reflux in 35 ml of dioxan for 2.5 hours. The reaction mixture is subsequently left to cool and it is poured into 250 ml of ice-water. The aqueous phase is washed twice with ether, acidified with 25% hydrochloric acid and extracted with ether. The ether phase obtained is washed with saturated sodium choride, dried over sodium sulphate and evaporated. By chromatography of the residue on silica gel while eluting with an elution mixture of hexane-ethyl acetate 2:1 to which is added 0.1% triethylamine there is obtained (all-E)-10-hydroxy-3,7,11-trimethyl-2,6,11-dodecatrienoic acid. IR (film): 3360 (OH); 2670, 2576, 1249 (CO$_2$H); 1691 (acid C=O); 1642 (C=C, conjugated); 900 (C=CH$_2$).

EXAMPLE 27

5.0 g (0.02 mol) of (all-E)-10-hydroxy-3,7,11-trimethyl-2,6,11-dodecatrienoic acid are stirred at room temperature for 6 hours together with 10.0 g of pyrolusite (precipitated, active) in 100 ml of methylene chloride, whereupon the mixture is suction filtered through Hyflo and the filtrate is evaporated. The residue is chromatographed on silica gel with hexane-ethyl acetate 1:1 with the addition of 0.1% triethylamine. There is obtained (all-E)-oxo-3,7,11-trimethyl-2,6,11-dodecatrienoic acid IR (film): 2559, 2482, 1254, (CO$_2$H), 1676 (acid C=O; C=O, conjugated), 1641 (C=C, conjugated).

EXAMPLE 28

31.55 g of isopropyl (all-E)-10-hydroxy-3,7,11-trimethyl-2,6,11-dodecatrienoate (0.107 mol) are added dropwise at 0° within 30 minutes to 360 ml of a 20% solution of diisobutylaluminium hydride (about 0.36 mol) in hexane. The mixture is subsequently stirred at 0° for a further 1 hour. 50 ml of methanol are then slowly added thereto at the same temperature, whereupon the mixture is poured into 1.5 l of ice-water. The mixture is subsequently made weakly acidic by means of 2N sulphuric acid, whereupon the organic phase is separated and the aqueous phase is extracted three times with 300 ml of ether each time. The combined hexane and ether phases are washed with 500 ml of saturated sodium chloride solution, dried over 50 g of sodium sulphate and evaporated. The crude product which remains behind as the residue is filtered over 250 g of silica gel with about 2 l of ethyl acetate-hexane 4:1. After evaporation and drying in a high vacuum there is obtained (all-E)-3,7,11-trimethyl-2,6,11-dodecatriene-1,10-diol as a colourless oil which crystallizes upon storage in a deep freezer (m.p. <30°).

EXAMPLE 29

A mixture of 13 g of (all-E)-3,7,11-trimethyl-2,6,11-dodecatriene-1,10-diol and 140 g of pyrolusite is stirred at room temperature for 1.5 hours in 1 l of n-hexane. After filtration and evaporation there are obtained 11.53 g of crude product which is chromatographed on silica gel firstly with hexane-ethyl acetate 2:1, then with hexane-ethyl acetate 1:1 with the addition of 0.1%. triethylamine. There is obtained (all-E)-10-hydroxy-3,7,11-trimethyl-2,6,11-dodecatrienal. IR (film): 3440 (OH), 1670 (aldehyde, conjugated), 897 (C=CH$_2$). MS: 218 (M—H$_2$O)$^+$.

EXAMPLE 30

26.0 g of (all-E)-3,7,11-trimethyl-2,6,11-dodecatriene-1,10-diol are added dropwise at room temperature to a suspension of 260 g of pyrolusite (precipitated, active) and 0.8 l of methylene chloride. After stirring for 3 hours the mixture is filtered through sodium sulphate and concentrated. The residue is added dropwise while stirring to a suspension of 260 g of pyrolusite (precipitated, active) and 0.8 l methylene chloride. The mixture is subsequently stirred at room temperature for a further 2 hours. After filtration and concentration there is obtained a crude product which is chromatographed on silica gel with hexane-ethyl acetate 2:1 with the addition of 0.1% triethylamine. There is obtained (all-E)-10-oxo-3,7,11-trimethyl-2,6,11-dodecatrienal. MS: 205 (M—CHO)$^+$.

EXAMPLE 31

4.33 g (18.3 mmol) of (all-E)-10-hydroxy-3,7,11-trimethyl -2,6,11-dodecatrienal are added dropwise at 0° to a Grignard solution prepared from 1.8 g (74 mmol) of magnesium and 10.24 g (72.6 mmol) of methyl iodide in 50 ml of absolute ether. After completion of the addition the mixture is stirred at room temperature overnight. 40 ml of a saturated solution of ammonium chloride are then added thereto and the mixture is stirred intensively, whereby a clear solution results. This solution is poured into 500 ml of a saturated solution of ammonium chloride, whereupon the mixture is extracted three times with ether. After washing the combined organic phases with saturated sodium chloride solution and filtration through sodium sulphate the filtrate is evaporated. The residue is chromatographed on silica gel with hexane-ethyl acetate 4:1 with the addition of 0.1% triethylamine. There is obtained (all-E)-4,8,12-trimethyl-3,7,12-tridecatriene-2,11-diol. MS: 234 $(M-H_2O)^-$, 216 $(M-2H_2O)^+$.

EXAMPLE 32

A solution of 2.64 g (11.2 mmol) of (all-E)-10-oxo-3,7,11-trimethyl-2,6,11-dodecatrienal is added dropwise at 0° to a mixture of 0.81 g (11.7 mmol) of hydroxylamine hydrochloride, 0.98 g (12 mmol) of sodium acetate, 10 ml of water and 50 ml of methanol. The mixture is subsequently stirred at 0° for a further 30 minutes. The reaction mixture is then concentrated, whereupon the residue is taken up in 100 ml of ether and washed with 200 ml of deionized water. The organic phase is firstly washed with saturated sodium chloride solution and then filtered through sodium sulphate. After evaporation the residue is chromatographed on silica gel with hexane-ethyl acetate 4:1 with the addition of 0.1% triethylamine, whereafter there is obtained (2E,6E)-3,7,11-trimethyl-10-oxo-2,6,11-dodecatrienal (E/Z)-oxime. wird. MS: 232 $(M-OH)^+$.

EXAMPLE 33

(a) A mixture of 50 g of pyrolusite (precipitated, active) and 5.0 g of isopropyl (all-E)-10-hydroxy-3,7,11-trimethyl-2,6,11-dodecatrienoate in 100 ml of methylene chloride is stirred at room temperature for 4 hours. The mixture is then filtered through Hyflo, whereupon the filtrate is evaporated and the residue is again treated with 100 ml of methylene chloride and 50 g of pyrolusite. After stirring for 4 hours the mixture is filtered and the filtrate is evaporated, whereafter a colourless oil remains behind as the residue. 3.1 g of this residue are chromatographed on silica gel with hexane-acetate 4:1 with the addition of 0.1% triethylamine, whereafter isopropyl (all -E)-10-oxo-3,7,11-trimethyl-2,6,11-dodecatrienoate is obtained. IR (film): 1711 (ester C=O), 1679 (ketone conjugated —CO), 1224, 1146 (ester).

(b) 10.0 g (94 mmol) of trimethyl orthoformate are added dropwise at room temperature within 20 minutes to a mixture of 20 g (68 mmol) of isopropyl (all-E)-10-oxo-3,7,11-trimethyl-2,6,11-dodecatrienoate, 10 ml of methanol and 100 mg of p-toluenesulfonic acid. The reaction mixture is subsequently stirred at room temperature for a further 4 hours and then poured into 500 ml of a saturated solution of sodium hydrogen carbonate. After three-fold extraction with ether the combined organic phases are firstly washed with saturated sodium chloride solution, then dried over sodium sulphate and evaporated. As the residue there remains behind isopropyl (all-E)-10,10-dimethoxy-3,7,11-trimethyl-2,6,11-dodecatrienoate as a colourless oil.

10.2 g of this oil are dissolved in 30 ml of absolute ether. 72 ml of a 20% solution of diisobutylaluminium hydride in toluene are then added dropwise at about 15° within 20 minutes. The mixture is subsequently stirred at room temperature for a further 3 hours. The reaction mixture is then cooled to 0° and treated cautiously firstly with 10 ml of ethyl acetate, then with 5 ml of methanol and finally with 50 ml of water and poured into a mixture of ice and saturated sodium chloride solution. After two-fold extraction with ether the combined organic phases are washed firstly with saturated sodium hydrogen carbonate solution and then with saturated sodium chloride solution. After drying over sodium sulphate and evaporation the residue is chromatographed on silica gel with hexane-ethyl acetate 2:1 with the addition of 0.1% triethylamine. There is obtained (all-E)-10,10-dimethoxy-3,7,11-trimethyl-2,6,11-dodecatrien-1-ol. MS: 251 $(M-OCH_3)^+$.

EXAMPLE 34

A mixture of 19.4 g (66 mmol) of isopropyl (all-E)-10-oxo-3,7,11-trimethyl-2,6,11-dodecatrienoate, 5.0 g (82 mmol) of 1,2-ethanediol, 100 mg of p-toluenesulfonic acid and 50 ml of toluene is boiled under reflux for 5 hours. The reaction mixture is then poured into 500 ml of a saturated solution of sodium hydrogen carbonate, whereupon the mixture is extracted three times with ether. The combined organic phases are washed with saturated sodium chloride solution, dried over sodium sulphate, filtered and evaporated, whereafter isopropyl (all-E)-3,7-dimethyl-9-[2-(1-methylvinyl)-1,3-dioxolan-2-yl]-2,6-nonadienoate is obtained in the form of a yellowish oil.

8.5 g of this oil are dissolved in 25 ml of absolute ether. 60 ml of a 20% solution of diisobutylaluminium hydride in toluene are then added dropwise thereto at about 15° within 20 minutes. After completion of the addition the mixture is stirred at room temperature for a further 2.5 hours. The reaction mixture is then cooled to 0° and treated slowly firstly with 10 ml of ethyl acetate, then with 5 ml of methanol and finally with 50 ml of water and subsequently poured into a mixture of ice and saturated sodium chloride solution. After two-fold extraction with ether the combined organic phases are washed firstly with saturated sodium hydrogen carbonate solution and then with saturated sodium chloride solution. After drying over sodium sulphate, filtration and evaporation the residue is chromatographed on silica gel with hexane-ethyl acetate 2:1 with the addition of 0.1% triethylamine, there being obtained (all-E)-3,7-dimethyl-9-[2-(1-methylvinyl)-1,3-dioxolan-2-yl]-2,6-nonadien-1-ol. MS: 239 $(M-CH_2=CH-CH_2-)^+$.

EXAMPLE 35

A mixture of 38.9 g (0.19 mol) of aluminum isopropylate, 50 ml of toluene and 37.4 g (0.15 mol) of 10,11-epoxy-1-methoxy-3,7,11-trimethyl-(2E,6E)-dodecadiene is boiled under reflux (bath temperature 140°) for 15 hours. The reaction mixture is then poured into 1.2 l of an ice-water mixture, acidified with 25% hydrochloric acid and extracted with hexane. The organic phase is washed firstly with saturated sodium bicarbonate solution and then with saturated sodium chloride solution, subsequently dried over sodium sulphate, filtered and evaporated. For purification, the residue is chromatographed on silica gel with hexane-diethyl ether 7:3, whereafter there is obtained (all-E)-12-methoxy-2,6,10-trimethyl-1,6,10-dodecatrien-3-ol. CI—MS (NH₃): 253 (M+H)⁺, 203 (M+H—(CH₃OH+H₂O))⁺.

EXAMPLE 36

A mixture of 5 g (15.8 mmol) of (all-E)-12-methoxy-2,6,10-trimethyl-1,6,10-dodecatrien-3-ol, 20 g of pyrolusite (precipitated, active) and 100 ml of methylene chloride is stirred at room temperature overnight. The mixture is then filtered, the filtrate is treated with 10 g of fresh pyrolusite, after stirring for 3 hours as well as after a further 1.5 hours and 3.5 hours, respectively, in each case a further 10 g of pyrolusite are added thereto and the mixture is subsequently stirred overnight. After filtration the filtrate is evaporated in a rotary evaporator. After drying in a high vacuum there is obtained (all-E)-12-methoxy-2,6,10-trimethyl-1,6,10-dodecatrien-3-one. MS: 218 (M—CH₃OH)⁺.

EXAMPLE 37

A mixture of 3.0 g (11 mmol) of (all-E/Z)-10,11-epoxy-3,7,11-trimethyl-1-(2-propynyloxy)-2,6-dodecadiene, 3.5 g (18 mmol) of aluminum isopropylate and 40 ml of toluene is boiled under reflux for 18 hours. The reaction mixture is then poured into a mixture of ice and 2N hydrochloric acid, whereupon the mixture is extracted twice with ether. The combined organic phases are washed firstly with saturated sodium hydrogen carbonate solution and then with saturated sodium chloride solution. After drying over sodium sulphate, filtration and concentration there is obtained a crude product which is chromatographed on silica gel with hexane-ethyl acetate 4:1 with the addition of 0.1% triethylamine. There is obtained (all-E/Z)-2,6,10-trimethyl-12-(2-propynyloxy)-1,6,10-dodecatrien-3-ol. CI—MS (NH₃): 277 (M+H)⁺, 259 (M+H—H₂O)⁺, 221 (M+H—HO—CH₂—C≡CH)⁺.

EXAMPLE 38

(a) A mixture of 5.7 g (20 mmol) of ethyl (E/Z)-10,11-epoxy-3,7,11-trimethyl-2-dodecenoate, 6.7 g (34 mmol) of aluminum isopropylate and 70 ml of toluene is boiled under reflux for 18 hours. The reaction mixture is then poured into a mixture of ice and 2N hydrochloric acid, whereupon the mixture is extracted twice with ether. The combined organic phases are washed firstly with saturated sodium hydrogen carbonate solution and then with saturated sodium chloride solution. After drying over sodium sulphate, filtration and evaporation there is obtained ethyl (E/Z)-10-hydroxy-3,7,11-trimethyl-2,11-dodecadienoate as a colourless oil.

(b) 60 ml of a 20% solution of diisobutylaluminium hydride are added dropwise at 10° within 30 minutes to a solution of 5.9 g of ethyl (E/Z)-10-hydroxy-3,7,11-trimethyl-2,11-dodecadienoate in 25 ml of absolute ether. The mixture is subsequently stirred at room temperature for a further 2 hours. The reaction mixture is then cooled to 0° and treated cautiously firstly with 6 ml of ethyl acetate, then with 3 ml of methanol and then with 25 ml of 25% hydrochloric acid and subsequently poured into a mixture of ice and saturated sodium chloride solution. After two-fold extraction with ether the combined organic phases are washed firstly with saturated sodium hydrogen carbonate solution and then with saturated sodium chloride solution, dried over sodium sulphate, filtered and evaporated. The residue is chromatographed on silica gel with hexane-ethyl acetate 1:1 with the addition of 0.1% triethylamine, whereafter (E/Z)-3,7,11-trimethyl-2,11-dodecadiene-1,10-diol is obtained as a colourless oil. MS: 222 (M—H₂O)⁺, 189 (M—(2H₂O+CH₃))⁺.

EXAMPLE 39

A mixture of 22.0 g (71 mmol) of tetrahydro-2-[(3,7,11-trimethyl-6,10-dodecadienyl)oxy]-2H-pyran, 80 ml of 1,2-dimethoxyethane and 16 ml of water is treated at —50° within 30 minutes with 13.5 g (76 mmol) of N-bromosuccinimide. The mixture is subsequently stirred at 0° for a further 2 hours and at room temperature for 30 minutes. The reaction mixture is then poured into ice-water, whereupon the mixture is extracted three times with ethyl acetate. The combined organic phases are washed firstly with saturated sodium hydrogen carbonate solution and then with saturated sodium chloride solution, dried over sodium sulphate, filtered and evaporated. There is obtained crude (E)-3-bromo-2,6,10-trimethyl-12-[(tetrahydro-2H)-pyran-2-yl)oxy]-6-dodecen-2-ol which is subsequently dissolved in 100 ml of methanol and treated at 0° with 14.0 g (0.1 mol) of potassium carbonate. After stirring at 0° for 15 hours the mixture is filtered over Hyflo, whereupon the filtrate is evaporated and the residue is taken up in 600 ml of ice-water and extracted three times with ether. The combined organic phases are washed with water, dried over sodium sulphate, filtered and evaporated. The residue is chromatographed on silica gel with hexane-ethyl acetate 4:1. There is obtained (E)-2-[(10,11-epoxy-3,7,11-trimethyl-6-dodecen-1-yl)oxy]tetrahydro-2H-pyran which is subsequently boiled under reflux for 18 hours together with 8.0 g (40 mmol) of aluminum isopropylate in 80 ml of toluene. The reaction mixture is then evaporated and the residue is taken up in 300 ml of 2N hydrochloric acid. After two-fold extraction with ether the combined organic phases are washed firstly with saturated sodium hydrogen carbonate solution and then with saturated sodium chloride solution, dried over sodium sulphate, filtered and evaporated. There is obtained (E)-2,6,10-trimethyl-12-[(tetrahydro-2H-pyran-2-yl)oxy]-1,6-dodecadien-3-ol which is dissolved in 130 ml of methanol and stirred at room temperature for 4 hours together with 13 g of strongly acidic ion-exchanger (Dowex 50 W X 8). After filtration and removal of the solvent in a rotary evaporator there remains behind a yellowish oil which is chromatographed on silica gel with hexane-ethyl acetate 2:1 with the addition of 0.1% triethylamine. There is obtained (E)-3,7,11-trimethyl-6,10-dodecadiene-1,10-diol in the form of a colourless oil. MS: 240 (M)⁺, 222 (M—H₂O)⁺.

EXAMPLE 40

(a) 9.54 g (113.4 mmol) of 3.4-dihydro-2H-pyran are added dropwise at 0° within 30 minutes to a mixture of 11.2 g (38 mmol) of isopropyl (all-E)-10-hydroxy-3,7,11-trimethyl-2,6,11-dodecatrienoate, 100 ml of methylene chloride and 1 g of pyridinium toluene-4-sulfonate, whereupon the mixture is stirred at room temperature for a further 2 hours. After concentration in a rotary evaporator the residue is taken up in water and extracted three times with hexane. The combined organic phases are washed with saturated sodium chloride solution, dried over sodium sulphate, filtered and evaporated. The residue is chromatographed on silica gel with hexane-ethyl acetate 9:1 with the addition of 0.1% conc. ammonia solution, whereafter there is obtained isopropyl (all-E)-3,7,11-trimethyl-10-[(tetrahydro-2H- pyran-2-yl)oxy]-2,6,11-dodecatrienoate. MS: 294 (M-dihydropyran, $C_5H_8O$)+, 276 (M-(2-hydroxy-tetrahydropyran, $C_5H_{10}O_2$))+.

(b) 600 ml of a 20% solution of diisobutylaluminium hydride are added dropwise at 10° within 1 hour to a solution of 66.2 g (0.17 mol) of crude isopropyl (all-E)-3,7,11-trimethyl-10-[(tetrahydro-2H-pyran-2-yl)oxy]-2,6,11-dodecatrienoate in 250 ml of diethyl ether. The mixture is subsequently stirred at room temperature for a further 2 hours. The reaction mixture is then cooled to 0° and treated cautiously firstly with 60 ml of ethyl acetate and then with 30 ml of methanol. This mixture is now poured into a saturated solution of potassium sodium tartrate. The mixture is then extracted twice with ether, whereupon the combined organic phases are washed firstly with saturated sodium hydrogen carbonate solution and then with saturated sodium chloride solution, dried over sodium sulphate, filtered and evaporated. The colourless oil which remains behind as the residue is chromatographed on silica gel with hexane-ethyl acetate 4:1 with the addition of 0.1% triethylamine. There is obtained (all-E)-3,7,11-trimethyl-10-[(tetrahydro-2H-pyran-2-yl)oxy]-2,6,11-dodecatrien-1-ol which is 98.6% pure in accordance with gas chromatography.

(c) A solution of 1.84 g (23.25 mmol) of absolute pyridine in 10 ml of absolute tetrahydrofuran is added dropwise at 0° to a mixture of 5 g (15.5 mmol) of (all-E)-3,7,11-trimethyl-10-[(tetrahydro-2H-pyran-2-yl)oxy]-2,6,11-dodecatrien-1-ol and 2.24 g (18.6 mmol) of pivaloyl chloride. The mixture is subsequently stirred at room temperature for a further 1 hour. The reaction mixture is then poured into 250 ml of an ice-water mixture, whereupon the mixture is extracted three times with hexane. The combined organic phases are washed with saturated sodium chloride solution, dried over sodium sulphate, filtered and evaporated. The colourless oil which remains behind as the residue is chromatographed on silica gel with hexane-ethyl acetate 9:1 with the addition of 0.1% triethylamine, whereafter there is obtained (all-E)-3,7,11-trimethyl-10-[(tetrahydro-2H-pyran-2-yl)oxy]-2,6,11-dodecatrienyl pivalate.

(d) A suspension of 5.5 g of strongly acidic ion-exchanger (Dowex 50 W 8 X) in 35 ml of methanol is treated at room temperature with 4.7 g of (all-E)-3,7,11-trimethyl-10-[(tetrahydro-2H-pyran-2-yl)oxy]-2,6,11-dodecatrienyl pivalate. The mixture is subsequently stirred at room temperature for a further 20 hours. After filtration and evaporation the residue is chromatographed on silica gel with hexane-ethyl acetate 4:1 with the addition of 0.1% triethylamine, whereafter there is obtained (all-E)-3,7,11-trimethyl-10-hydroxy-2,6,11-dodecatrienyl pivalate. MS (CI with $NH_3$): 305 (M+H)—$H_2O$)+, 221 ((M+H)—($CH_3)_3CCO_2H$)+.

EXAMPLE 41

A mixture of 26 g (0.1 mol) of ethyl (all-E)-3,7,11-trimethyl-2,4,6,10-dodecatetraenoate, 180 ml of 1,2-dimethoxyethane and 40 ml of water is treated at −5° within 20 minutes with 20 g (0.112 mol) of N-bromosuccinimide. After stirring for 3 hours at −5° the mixture is treated with 5 g of sodium sulphate and 10 g of potassium carbonate and subsequently stirred for a further 10 minutes. After removing the solids by filtration the filtrate is treated with 18 g (0.13 mol) of potassium carbonate and stirred at 0° for 12 hours. The reaction mixture is then concentrated, treated with 200 ml of ice-water and extracted twice with 100 ml of ether each time. The combined organic phases are dried over sodium sulphate, filtered and evaporated, and the yellow oil obtained is chromatographed on silica gel with hexane-ethyl acetate 95:5. There is obtained ethyl (all-E)-10,11-epoxy-3,7,11-trimethyl-2,4,6-dodecatrienoate which is subsequently boiled under reflux for 15 hours together with 8.4 g (40.8 mmol) of aluminum isopropylate in 170 ml of toluene. The reaction mixture is then poured into 150 ml of ice-water, adjusted to pH 4 with 25% hydrochloric acid solution and extracted with ether. The ether phase is washed with ice-water and then with saturated sodium chloride solution, dried over sodium sulphate, filtered and concentrated. The residual yellow oil is chromatographed on silica gel with hexane-ethyl acetate 8:2 with the addition of 0.1% triethylamine, whereafter there is obtained isopropyl (all-E)-10-hydroxy-3,7,11-trimethyl-2,4,6,11-dodecatetraenoate. MS: 292 (M)+, 232 (M—($CH_3)_2CH$—OH)+.

(b) 57 ml (85 mmol) of a 20% solution of diisobutylaluminum hydride in hexane are added dropwise at −5° to a solution of 5 g (17.1 mmol) of isopropyl (all-E)-10-hydroxy-3,7,11-trimethyl-2,4,6,11-dodecatetraenoate in 20 ml of hexane. Thereafter, the reaction mixture is treated with 250 ml of 20% sodium hydroxide solution, whereupon the mixture is extracted with ether. The ether phase is washed firstly with saturated sodium hydrogen carbonate solution and then with water, dried over sodium sulphate and concentrated. The residue is chromatographed on silica gel with hexane-ethyl acetate 1:1 with the addition of 0.1% triethylamine, whereafter there is obtained white, waxy (all-E)-3,7,11-trimethyl-2,4,6,11-dodecatetraene-1,10-diol of m.p. 53°–54°.

EXAMPLE 42

(a) 58.8 g (0.33 mol) of N-bromosuccinimide are added at −5° within 30 minutes to a mixture of 90.4 g (0.295 mol) of (all-E)-farnesyl tetrahydropyranyl ether, 600 ml of 1,2-dimethoxyethane and 120 ml of water. The mixture is subsequently stirred at room temperature for a further 1 hour. The mixture is then poured into 2 l of water, whereupon the mixture is extracted three times with 650 ml of ethyl acetate each time. The combined organic phases are washed with saturated sodium chloride solution, dried over sodium sulphate and evaporated. There is obtained crude (all-E)-3,bromo-2,6,10-trimethyl-12-[(tetrahydro-2H-pyran-2-yl)oxy]-6,10-dodecadien-2-ol.

The above crude product is added dropwise within 5 minutes to a mixture of 30 g of potassium carbonate and 250 ml of methanol, whereupon the mixture is stirred at room temperature for a further 1 hour and then concentrated. The residue is taken up in ether and washed firstly with water and then with saturated sodium chloride solution. After drying over sodium sulphate and concentration there is obtained (2E,6E)-10,11-epoxy-farnesyl tetrahydropyranyl ether. MS (CI with $NH_3$): 221 (M+H-(2-hydroxy-tetrahydropyran, $C_5H_{10}O$))+; IR (film) 1668 (—C=C—), 1378, 1359 (gem. dimethyl), 870 (epoxide).

(b) 95 g (0.295 mol) of (2E,6E)-10,11-epoxy-farnesyl tetrahydropyranyl ether are added at 110° within 5 minutes to a mixture of 60 g (0.294 mol) of aluminum ispropylate and 600 ml of toluene. The mixture is then boiled under reflux for 20 hours. The reaction mixture is subsequently poured into 2 l of ice-water and adjusted to pH 5 by the addition of ice-cold 2N hydrochloric acid. After three-fold extraction with hexane the combined organic phases are washed with saturated sodium chloride solution, filtered over sodium sulphate and then evaporated. The separated pale yellow oil is chromatographed on silica gel with hexane-ethyl acetate 4:1 with the addition of 0.1% triethylamine. After concentration and drying in a high vacuum there is obtained (all-E)-2,6,10-trimethyl-12-[(tetrahydro-2H-pyran-2-yl)oxy]-1,6,10-dodecatrien-3-ol.

(c) 50.4 g (0.156 mol) of (all-E)-2,6,10-trimethyl-12-[(tetrahydro-2H-pyran-2-yl)oxy]-1,6,10-dodecatrien-3-ol are added dropwise within 10 minutes to a mixture of 500 g of manganese dioxide and 1.5 l of methylene chloride. The mixture is stirred at room temperature for a further 20 hours and then filtered over a layer of sodium sulphate. After evaporation of the filtrate there is obtained (all-E)-2,6,10-trimethyl-12-[(tetrahydro-2H-pyran-2-yl)oxy]-1,6,10-dodecatrien-3-one.

The above product is added dropwise within 10 minutes to a mixture of 70 g of Dowex 50 W X 8 and 500 ml of methanol. The mixture is stirred at room temperature for 2 hours, then filtered through a suction filter and the filtrate is subsequently evaporated. The residue is chromatographed on silica gel with hexane-ethyl acetate 1:1 with the addition of 0.1% triethylamine. After concentration of the eluate and drying in a high vacuum there is obtained pure (all-E)-12-hydroxy-2,6,10-trimethyl-1,6,10-dodecatrien-3-one. IR (film): 3398, 1003 (OH), 3097 (C=$CH_2$), 1675 (ketone conj.), 1630 (—C=C—, conj.), 1368 (gem. dimethyl).

EXAMPLE 43

752 mg (9.5 mmol) of absolute pyridine are added dropwise at 0° to a mixture of 1.5 g (6.34 mmol) of (all-E)-12-hydroxy-2,6,10-trimethyl-1,6,10-dodecatrien-3-one and 776 mg (7.6 mmol) of acetic anhydride. The reaction mixture is subsequently stirred at 0° for 30 minutes, whereupon it is poured into 250 ml of ice-water while stirring vigorously. After three-fold extraction with hexane the combined organic phases are washed with saturated sodium chloride solution, dried over sodium sulphate and then concentrated. The residue is chromatographed on silica gel with hexane-ethyl acetate 4:1 with the addition of 0.1% triethylamine, whereafter there is obtained (all-E)-3,7,11-trimethyl-10-oxo-2,6,11-dodecatrienyl acetate. MS (CI with $NH_3$): 296 $(M+NH_4)^+$.

EXAMPLE 44

A mixture of 5.29 g (22.4 mmol) of (all-E)-12-hydroxy-2,6,10-trimethyl-1,6,10-dodecatrien-3-one, 1.59 g (22.8 mmol) of hydroxylamine hydrochloride, 0.96 g (24.0 mmol) of solid sodium hydroxide, 80 ml of methanol and 10 ml of water is stirred at room temperature for 20 hours. The mixture is then concentrated and the residue is taken up in a mixture of 50 ml of water and 50 ml of ether. After shaking vigorously in a separating funnel the ether phase is separated. The aqeuous phase is subsequently extracted three times with ether. The combined ether phases are dried over sodium sulphate, filtered and evaporated. The residue is chromatographed on silica gel with hexane-ethyl acetate 4:1 with the addition of 0.1% triethylamine, and there is obtained (6E,10E)-12-hydroxy-2,6,10-trimethyl-1,6,10-dodecatrien-3-one oxime. MS: 234 $(M—OH)^+$.

EXAMPLE 45

2.80 g (10 mmol) of (all-E)-4,8-dimethyl-10-[(tetrahydro-2H-pyran-2-yl)oxy]-4,8-decadienal are added dropwise at −70° to a Grignard solution prepared from 350 mg (14.4 mmol) of magnesium and 1.83 g (12 mmol) of freshly distilled n-phenyl bromide in 10 ml of absolute tetrahydrofuran. The mixture is subsequently left to warm to 0° and is stirred at this temperature for a further 30 minutes. The reaction mixture is then poured into 250 ml of saturated ammonium chloride solution of 0°. After three-fold extraction with ether the combined organic extracts are washed with saturated sodium chloride solution and then filtered over sodium sulphate. After concentration the residue is chromatographed on silica gel with hexane-ethyl acetate 4:1, whereafter there is obtained (all-E)-9,13-dimethyl-15-[(tetrahydro-2H-pyran-2-yl)oxy]-9,13-pentadecadien-6-ol.

The above material is stirred at 55° for 1 hour together with 300 mg of pyridinium toluene-4-sulfonate in 50 ml of absolute ethanol. The mixture is then evaporated and the residue is taken up in 300 ml of water. After three-fold extraction with ether the ether phase is washed with saturated sodium chloride solution and then dried over sodium sulphate. After concentration the residue is chromatographed on silica gel with hexane-ethyl acetate 7:3. The (all-E)-3,7-dimethyl-2,6-pentadecadiene-1,10-diol obtained is dried in a high vacuum. MS: 250 $(M—H_2O)^+$.

EXAMPLE 46

(a) A solution of 3.92 g (151 mmol) of acetylene in 70 ml of absolute tetrahydrofuran is treated dropwise in an argon atmosphere at −70° firstly with 87.2 ml (140 mmol) of a 1.6M solution of butyllithium in hexane and then with a solution of 13.28 g (47.4 mmol) of (all-E)-4,8-dimethyl-10-[(tetrahydro-2H-pyran-2-yl)oxy]4,8-decadienal in 60 ml of absolute tetrahydrofuran. The mixture is subsequently stirred at −70° for a further 1 hour and then at −30° for 30 minutes. After warming to 0° the reaction mixture is poured into a mixture of saturated ammonium chloride solution and ice. After separating the organic phase the aqueous phase is extracted three times with ether. The combined organic phases are washed with saturated sodium chloride solution, filtered over sodium sulphate and then concentrated. The residue is chromatographed on silica gel with hexane-ethyl acetate 4:1, whereafter there is obtained (all-E)-6,10-dimethyl-12-[(tetrahydro-2H-pyran-2-yl)oxy]-6,10-dodecadien-1-yn-3-ol.

(b) 6.65 g (21.7 mmol) of (all-E)-6,10-dimethyl-12-[(tetrahydro-2H-pyran-2-yl)oxy]-6,10-dodecadien-1-yn-3-ol are added dropwise at room temperature within 5 minutes to a suspension of 10 g of Dowex 50 W X 8 in 60 ml of absolute methanol. After stirring for 3 hours the mixture is filtered and the filtrate is concentrated. The residue is chromatographed on silica gel with hexane-ethyl acetate 1:1 with the addition of 0.1% triethylamine, and there is obtained (all-E)-3,7-dimethyl-2,6-dodecadien-11-yne-1,10-diol as a colourless oil. IR (film): 3346, 1065, 1004 (OH), 3296, 2113 (—C≡CH), 1667 (—C=C—), 1384 (gem. dimethyl), 653, 629 (—C≡CH). MS: 204 $(M—H_2O)^+$.

EXAMPLE 47

(a) A solution of 13.07 g (42.65 mmol) of (all-E)-6,10-dimethyl-12-[(tetrahydro-2H-pyran-2-yl)oxy]-6,10-dodecadien-1-yn-3-ol in 50 ml of methylene chloride is added dropwise at 0° to a suspension of 130 g of pyrolusite (active, precipitated) in 400 ml of methylene chloride. The mixture is then stirred overnight at +4°. A further 13 g of pyrolusite are subsequently added thereto and the mixture is stirred at room temperature for 1 hour. The mixture is then filtered over a layer of sodium sulphate and concentrated. The residue is chromatographed on silica gel with hexane-ethyl acetate 4:1, whereafter there is obtained (all-E)-6,10-dimethyl-12-[(tetrahydro-2H-pyran-2-yl)oxy]-6,10-dodecadien-1-yn-3-one.

(b) A solution of 7.7 g (25.3 mmol) of (all-E)-6,10-dimethyl-12-[(tetrahydro-2H-pyran-2-yl)oxy]-6,10-dodecadien-1-yn-3-one in 10 ml of absolute ethanol is added dropwise at 55° to a solution of 800 mg of pyridinium toluene-4-sulfonate in 100 ml of absolute ethanol. Afer 1.5 hours the mixture is concentrated and the residue is taken up in ether. The ether phase is washed firstly with water and then with saturated sodium chloride solution. Thereupon, the mixture is filtered over sodium sulphate and the filtrate is concentrated. By chromatography of the residue on silica gel with hexane-ethyl acetate 1:1 there is obtained firstly (all-E)-10,10-diethoxy-3,7-dimethyl-2,6-dodecadien-11-yn-1-ol (MS: 249 (M—OEt)+), followed by (all-E)-12-hydroxy-6,10-dimethyl-6,10-dodecadien-1-yn-3-one (IR (film): 3358, 1002 (OH), 3258, 2090 (—C≡CH), 1680 (ketone conj.)).

EXAMPLE 48

(a) A solution of 0.98 g (12 mmol) of 3,3-dimethyl-1-butyne in 25 ml of absolute tetrahydrofuran is treated dropwise in an argon atmosphere at −70° firstly with 7.5 ml (12 mmol) of a 1.6M solution of butyllithium in hexane and then with 2.8 g (10 mmol) of (all-E)-4,8-dimethyl-10-[(tetrahydro-2H-pyran-2-yl)oxy]-4,8-decadienal. Thereupon, the mixture is stirred firstly at −70° for a further 1 hour and then at room temperature for 15 hours. The reaction mixture is subsequently poured into 250 ml of ice-cold saturated ammonium chloride solution, whereupon the mixture is extracted three times with ether. The combined organic phases are washed with saturated sodium chloride solution, filtered over sodium sulphate and then concentrated. The residue is chromatographed on silica gel with hexane-ethyl acetate 4:1 with the addition of 0.1% triethylamine, whereafter there is obtained (all-E)-2,2,8,12-tetramethyl-14-[(tetrahydro-2H-pyran-2-yl)oxy]-8,12-tetradecadien-3-yn-5-ol. MS: 278 (M-dihydropyran, $C_5H_8O$)+, 260 (M-(dihydropyran+$H_2O$))+.

(b) 2.92 g of (all-E)-2,2,8,12-tetramethyl-14-[(tetrahydro-2H-pyran-2-yl)-oxy]-8,12-tetradecadien-3-yn-5-ol are added dropwise at 0° within 5 minutes to a suspension of 29.2 g of manganese dioxide (activated) in 100 ml of methylene chloride. The reaction mixture is subsequently stirred at room temperature for a further 30 minutes, whereupon it is suction filtered over a layer of sodium sulphate and the filtrate is concentrated. The residue is chromatographed on silica gel with hexane-ethyl acetate 4:1, whereafter there is obtained (all-E)-2,2,8,12-tetramethyl-14-[(tetrahydro-2H-pyran-2-yl)oxy]-8,12-tetradecadien-3-yn-5-one.

(c) A mixture of 70 ml of 90% ethanol, 0.246 g of pyridinium toluene-4-sulfonate and 2.45 g (6.8 mmol) of (all-E)-2,2,8,12-tetramethyl-14-[(tetrahydro-2H-pyran-2-yl)oxy]-8,12-tetradecadien-3-yn-5-one is heated to 55° for 17 hours. After concentration the residue is taken up in water, whereupon the mixture is extracted with ether. The combined organic extracts are washed with saturated sodium chloride solution and then suction filtered over a layer of sodium sulphate. After concentration of the filtrate the residue is chromatographed on silica gel with hexane-ethyl acetate 4:1. There is obtained (all-E)-14-hydroxy-2,2,8,12-tetramethyl-8,12-tetradecadien-3-yn-5-one. MS: 243 (M—($CH_3$+$H_2O$))+.

EXAMPLE 49

(a) 120 ml (0.19 mol) of a 1.7M solution of butyllithium in hexane are added dropwise at −70° within 25 minutes to 190 ml (0.32 mol) of an about 1.7M solution of propyne in tetrahydrofuran. After stirring at −70° for 30 minutes there is added dropwise at the same temperature within 10 minutes a solution of 30.81 g (0.11 mol) of (all-E)-4,8-dimethyl-10-[(tetrahydro-2H-pyran-2-yl)oxy]-4,8-decadienal in 30 ml of abs. tetrahydrofuran. The mixture is then stirred at −70° for a further 1 hour. After warming to room temperature the mixture is poured into 1.5 l of a saturated solution of ammonium chloride in water. After three-fold extraction with n-hexane the extracts are combined, dried with sodium sulphate, filtered and concentrated, there being obtained crude (all-E)-7,11-dimethyl-13-[(tetrahydro-2H-pyran-2-yl)oxy]-7,11-tridecadien-2-yn-4-ol.

(b) 7.9 g (24.65 mmol) of (all-E)-7,11-dimethyl-13-[(tetrahydro-2H-pyran-2-yl)oxy]-7,11-tridecadien-2-yn-4-ol are added dropwise at room temperature to a mixture of 10 g of strongly acidic ion-exchanger (Dowex 50 W 8 X) and 60 ml of absolute methanol. The mixture is subsequently stirred at room temperature for a further 2.5 hours. The mixture is then filtered through a glass frit and the filtrate is evaporated. The residue is chromatographed on 200 g of silica gel with hexane-ethyl acetate 1:1 with the addition of 0.1% triethylamine. There is obtained (all-E)-3,7-dimethyl-2,6-tridecadien-11-yn-1,10-diol. MS (CI with $NH_3$): 254 (M+$NH_4$)+.

EXAMPLE 50

(a) 20.5 g (67 mmol) of (all-E)-7,11-dimethyl-13-[(tetrahydro-2H-pyran-2-yl)oxy]-7,11-tridecadien-yn-4-ol are added dropwise at 0° within 15 minutes to a suspension of 200 g of manganese dioxide (active, precipitated) in 800 ml of methylene chloride. After warming to room temperature the mixture is stirred for a further 2.5 hours. The mixture is then filtered and the filtrate is concentrated. The residue is chromatographed on silica gel with hexane-ethyl acetate 4:1. There is obtained (all-E)7,11-dimethyl-13-[(tetrahydro-2H-pyran-2-yl)oxy]-7,11-tridecadien-2-yn-4-one.

(b) 15.13 g (47.8 mmol) of (all-E)-7,11-dimethyl-13-[(tetrahydro-2H-pyran-2-yl)oxy]-7,11-tridecadien-2-yn-4-one are added dropwise at 55° to a solution of 1.5 g of pyridinium toluene-4-sulfonate in 200 ml of absolute ethanol. The mixture is subsequently stirred at the same temperature for a further 2 hours. After concentrating the reaction mixture the residue is taken up in ether and extracted with 500 ml of water. After separating the ether phase the aqueous phase is again extracted with ether. The combined organic phases are washed with saturated sodium chloride solution, dried over sodium sulphate and then concentrated. The residue is chromatographed on silica gel firstly with hexane-ethyl acetate 4:1, and then 1:1, whereafter there is obtained (all-E)-13-hydroxy-7,11-dimethyl-7,11-tridecadien-2-yn-4-one. MS: 201 (M—($CH_3$+$H_2O$))+; IR (film): 3412 (OH), 2219 (—C≡C—), 1670 (ketone conj.).

EXAMPLE 51

A solution of 9.6 g (30 mmol) of (all-E)-7,11-dimethyl-13-[(tetrahydro-2H-pyran-2-yl)oxy]-7,11-tridecadien-2-yn-4-ol in 50 ml of absolute tetrahydrofuran is treated dropwise at room temperature with 30 ml (105 mmol) of an about 3.5M solution of sodium dihydro-bis-(2-methoxyethoxy)-aluminate in toluene. The mixture is then boiled at 110° for 1 hour. Subsequently, the reaction mixture is carefully poured on to ice, whereafter ice-cold 2N hydrochloric acid is added up to a slightly acidic reaction. The mixture is then extracted three times with hexane and the combined hexane phases are washed neutral with saturated sodium chloride solution. After drying over sodium sulphate, filtration and evaporation there is obtained (all-E)-7,11-dimethyl-13-[(tetrahydro-2H-pyran-2-yl)oxy]-2,7,11-tridecatrien-4-ol.

The above material is boiled at 55° for 1.5 hours together with 750 mg of pyridinium toluene-4-sulfonate in 200 ml of absolute ethanol. The mixture is then evaporated and the residue is taken up in ether. The organic phase is washed with water and then with saturated sodium chloride solution and subsequently filtered over sodium sulphate. After concentration of the filtrate the residue is chromatographed on silica gel with hexane-ethyl acetate 1:1. There is obtained (all-E)-3,7-dimethyl-2,6,11-tridecadien-triene-1,10-diol. MS: 189 (M—(C-H$_2$OH+H$_2$O))$^+$.

EXAMPLE 52

(a) A mixture of 4.8 g (200 mmol) of magnesium and 200 ml of absolute tetrahydrofuran is treated at 70°–80° with about 200 mg of iodine crystals. After the iodine colour has disappeared 24 g (178 mmol) of 2-methyl-1-bromopropene are added dropwise. The mixture is then boiled under reflux for a further 2 hours. After cooling to room temperature the Grignard solution obtained is filtered in an argon atmosphere, cooled to about −70° and treated dropwise with a solution of 24 g (85 mmol) of (all-E)-4,8-dimethyl-10-[(tetrahydro-2H-pyran-2-yl)oxy]-4,8-decadienal in 50 ml of tetrahydrofuran. After completion of the addition the mixture is stirred at a temperature of −60° to −70° for a further 2 hours. The cooling is then removed and the mixture is stirred at room temperature overnight. After the addition of 100 ml of saturated ammonium chloride solution the organic phase is separated. The aqueous phase is extracted twice with ether. The combined organic phases are dried over magnesium sulphate and concentrated. The residue is chromatographed on silica gel with hexane-ethyl acetate 4:1. There is obtained (all-E)-2,7,11-trimethyl-13-[(tetrahydro-2H-pyran-2-yl)oxy]-2,711-tridecatrien-4-ol. MS: 234 (M-(2-hydroxy-tetrahydropyran, C$_5$H$_{10}$O$_2$))$^+$.

(b) A mixture of 3 g (8.91 mmol) of (all-E)-2,7,11-trimethyl-13-[(tetrahydro-2H-pyran-2-yl)oxy]-2,7,11-tridecadien-trien-4-ol, 54 ml of ethanol, 16 ml of water and 0.5 g of pyridinium toluene-4-sulfonate is boiled at 55° for 1 hour. The mixture is then concentrated, treated with toluene and again evaporated. The residue is taken up in ether and filtered through a suction filter coated with silica gel. After concentrating the filtrate the residue is chromatographed on silica gel with hexane-ethyl acetate 1:1. There is obtained (all-E)-3,7,12-trimethyl-2,6,11-tridecatriene-1,10-diol. MS: 216 (M—2H$_2$O)$^+$.

EXAMPLE 53

(a) 12.51 ml of 1,8-diazabicyclo[5.4.0]undec-7-ene are added to a solution of 11.72 g of tert.-butyldimethylchlorosilane in 140 ml of dichloromethane. 20.6 g of isopropyl (all-E)-10-hydroxy-3,7,11-trimethyl-2,6,11-dodecatrienoate are subsequently added dropwise thereto within 30 minutes. After stirring at room temperature for 28 hours the reaction mixture is poured into ice-water and extracted twice with 400 ml of ethyl acetate each time. The combined extracts are washed with saturated sodium chloride solution, dried over sodium sulphate, filtered and evaporated. The oil obtained is chromatographed on 1.5 kg of silica gel with hexane-2% ethyl acetate. There is thus obtained isopropyl (6E)-10-(tert.-butyldimethylsiloxy)-3,7,11-trimethyl-2,6,11-dodecatrienoate as a yellowish oil.

(b) 24.5 ml of sodium dihydro-bis(2-methoxyethoxy)-aluminate (70% solution in toluene, "Vitride") are slowly added dropwise at 0° to a solution of 32.6 g of isopropyl (6E)-10-(tert.-butyldimethylsiloxy)-3,7,11-trimethyl-2,6,11-dodecatrienoate in 80 ml of hexane. After stirring at room temperature for 2 hours a further 2.5 ml of "Vitride" are added dropwise. The reaction mixture is stirred for a further hour and then treated cautiously with 20 ml of water, whereupon the mixture is poured into ice-water. After adding 70 ml of 50% sulphuric acid the mixture is extracted twice with hexane. The combined extracts are washed with 2N sulphuric acid, water, saturated sodium bicarbonate solution and saturated sodium chloride solution, dried over sodium sulphate, filtered and evaporated. The residue is chromatographed on silica gel with hexane-ethyl acetate-triethylamine 80:20:0.1, whereby (6E)-10-(tert.-butyldimethylsiloxy)-3,7,11-trimethyl-2,6,11-dodecatrien-1-ol is obtained as a colourless oil. NMR (80 MHz, CDCl$_3$); 5.45 (t, J=7.1 olefin. H); 5.15 (m, 1 olefin. H); 4.95–4.75 (m, 2H-C(12)); 4.2 (d, J=7, 2H-C(1)); 4.05 (t, J=6.5, H-C(10)); 2.2–1.3 (m, 4CH$_2$, 3CH$_3$); 0.9 (s, SiC(CH$_3$)$_3$); 0.05 and 0.0 (2s, Si(CH$_3$)$_2$).

(c) 10.58 g of (6E)-10-(tert.-butyldimethylsiloxy)-3,7,11-trimethyl-2,6,11-dodecatrien-1-ol are added dropwise at 0° to a suspension of 110 g of manganese dioxide (precipitated, active) in 220 ml of dichloromethane and the mixture is stirred at room temperature for 2 hours. After filtration over Hyflo the filtrate is concentrated and oily residue is chromatographed on silica gel with hexane-ethyl acetate-triethylamine 90:10:0.1. There is obtained (6E)-10-(tert.-butyldimethylsiloxy)-3,7,11-trimethyl-2,6,11-dodecatrienal as a yellowish oil. NMR (80 MHz, CDCl$_3$): 10.1 (d, J=8, H-C(1)); 6.0 (d, J=8, H-C(2)); 5.2 (m, H-C(6)); 5.0–4.8 (m, 2H-C(12)); 4.1 (t, J=6.5, H-C(10)); 2.4–1.4 (m, 4CH$_2$, 3CH$_3$); 0.95 (s, SiC(CH$_3$)$_3$); 0.1 and 0.05 (2s, Si(CH$_3$)$_2$).

(d) A solution of 7.3 g of (6E)-10-(tert.-butyldimethylsiloxy)-3,7,11-trimethyl-2,6,11-dodecatrienal in 10 ml of ether is added dropwise at −20° to a methylmagnesium iodide solution prepared from 0.56 g of magnesium shavings and 3.1 g of methyl iodide in 80 ml of ether. After stirring at −20° for 2 hours the reaction mixture is poured into a mixture of ice and saturated ammonium chloride solution and extracted twice with ether. The combined organic extracts are washed with saturated sodium chloride solution, dried over sodium sulphate, filtered and evaporated. The oil which remains behind as the residue is chromatographed on silica gel with hexane-ethyl acetate-triethylamine 90:10:0.1, whereby (7E)-11-(tert.-butyldimethylsiloxy)-4,8,12-trimethyl-3,7,12-tridecadien-trien-2-ol is obtained as a colourless oil. NMR (250 MHz, CDCl$_3$): 5.2 (d, J=8 H-C(3)); 5.1 (t, J=6.5, H-C(7)); 4.84 and 4.75 (2m, 2H-C(13)); 4.57 (m, H-C(2)); 4.0 (t, J=6.5, H-C(11)); 2.25–1.4 (m, 4CH$_2$, 3CH$_3$); 1.22 (d, J=6.5, 3H-C(1)); 0.89 (s, SiC(CH$_3$)$_3$); 0.04 and 0.0 (2s, Si(CH$_3$)$_2$).

(e) 5 g of (7E)-11-(tert.-butyldimethylsiloxy)-4,8,12-trimethyl-3,7,12-tridecatrien-2-ol are added dropwise at 0° to a suspension of 25 g of manganese dioxide (active, precipitated) in 50 ml of dichloromethane. After stirring at room temperature for 5 hours the reaction mixture is filtered over sodium sulphate and the filtrate is evaporated. The material obtained is subjected twice more to the same oxidation process with fresh manganese dioxide each time in order to achieve complete reaction. Chromatography of the crude product obtained on silica gel with hexane-ethyl acetate 2%→5% yields (7E)-11-(tert.-butyldimethylsiloxy)-4,8,12-trimethyl-3,7,12-tridecatrien-2-one as a yellowish which has a purity of 95% in accordance with a gas chromatography. NMR (250 MHz, CDCl$_3$): 6.05 (s, H-C(3)); 5.1 (m, H-C(7)); 4.84 and 4.75 (2m, 2H-C(13)); 4.0 (t, J=6.5, H-C(11)); 2.3–1.4 (m, 4CH$_2$, 3CH$_3$); 0.89 (s, SiC(CH$_3$)$_3$); 0.35 and 0.0 (2s, Si(CH$_3$)$_2$).

(f) 13 ml of 2N HCl are added at 0° to a solution of 3.2 g of (7E)-11-(tert.-butyldimethylsiloxy)-4,8,12-trimethyl-3,7,12-tridecatrien-2-one in 70 ml of tetrahydrofuran and 35 ml of methanol, whereupon the mixture is stirred at room temperature for 5.5 hours. Thereupon, the reaction mixture is poured into 300 ml of water and extracted twice with hexane. The combined extracts are washed with saturated sodium bicarbonate solution and saturated sodium chloride solution, dried over sodium sulphate, filtered and evaporated. Chromatography of the residue on silica gel with hexane-ether 6:4 yields (3E/Z,7E)-11-hydroxy-4,8,12-trimethyl-3,7,12-tridecatrien-2-one as a slightly yellowish oil. In accordance with gas chromatography it is a (Z/E) mixture in the ratio of 1:2. NMR (250 MHz, CDCl$_3$): 6.06 (s, H-C(3)); 5.13 (m, H-C(7)); 4.94 and 4.84 (2s, 2H-C(13)); 4.05 (t, J=6, H-C(11)); 2.6 (t, 2H-C(5) from the 3Z-isomer); 2.17 and 2.16 (2s, CH$_3$CO from the 3E- and 3Z-isomers); 2.12 and 1.87 (2s, CH$_3$-C(4) from the 3E and 3Z-isomers); 2.0 (m, 2CH$_2$); 1.75–1.5 (m, 2CH$_2$, 2CH$_3$). IR (film): 3434 (broad, OH); 1685 (conj. ketone); 1613 (conj. C=C); 897 (=CH$_2$). MS: 232 (1, M$^+$—H$_2$O); 217 (2, M$^+$—H$_2$O—CH$_3$); 189 (5, M$^+$—H$_2$O—COCH$_3$); 43 (100, COCH$_3$). Analysis: C$_{16}$H$_{26}$O$_2$ (250.38); Calc. C 76.75, H 10.47%. found C 76.55, H 10.62%.

EXAMPLE 54

(a) A suspension of 400 g of manganese dioxide (activated) in 1 l of methylene chloride is treated at room temperature with 10 g (30 mmol) of (all-E)-2,7,11-trimethyl-13-[(tetrahydro-2H-pyran-2-yl)oxy]-2,7,11-tridecatrien-4-ol. The mixture is subsequently stirred at room temperature for a further 2 hours. It is then filtered over a Hyflo layer. After concentrating the filtrate the residue is chromatographed on silica gel (0.040–0.063 mm) under a pressure of about 0.1 bar (compressed air) with hexane-ethyl acetate firstly in the ratio 9:1 and then in the ratio 8:2. After concentrating the filtrate and drying the residue in a high vacuum there is obtained (all-E)-2,7,11-trimethyl-13-[(tetrahydro-2H-pyran-2-yl)oxy]-2,7,11-tridecatrien-4-one. MS: 232 (M-(2-hydroxy-tetrahydropyran, C$_5$H$_{10}$O$_2$))$^+$.

(b) A mixture of 2 g of strongly acidic ion-exchanger (Dowex 50 W 8 X), 100 ml of ethanol and 3.3 g of (all-E)-2,7,11-trimethyl-13-[(tetrahydro-2H-pyran-2-yl)oxy]-2,7,11-tridecatrien-4-one is stirred at room temperature for 3 hours. After filtration and concentration of the filtrate the residue is chromatographed on silica gel with hexane-ethyl acetate 3:2, whereafter (all-E)-13-hydroxy-2,7,11-trimethyl-2,7,11-tridecatrien-4-one is obtained in the form of a slightly yellow oil. IR (film): 3420, 1009 (OH), 1686 (ketone conj.), 1619 (C=C conj), 1382, 1358, (gem. dimethyl).

EXAMPLE 55

(a) 35 ml of a 4.3 molar solution of vinyl bromide (150 mmol) in tetrahydrofuran are added dropwise at 60° to a suspension of 2 g (83 mmol) of magnesium in 50 ml of tetrahydrofuran previously distilled over sodium. The mixture is then boiled under reflux for a further 30 minutes. After cooling to −5° the mixture is treated dropwise with a solution of 10 g (36 mmol) of (all-E)-4,8-dimethyl-10-[(tetrahydro-2H-pyran-2-yl)oxy]-4,8-decadienal in 50 ml of absolute tetrahydrofuran. After completion of the addition (about 20 minutes) the mixture is stirred at 0° for a further 1 hour. The reaction mixture is then poured into 500 ml of a saturated solution of ammonium chloride. After three-fold extraction with ether the combined organic phases are washed firstly with saturated sodium hydrogen carbonate solution and then with saturated sodium chloride solution. After drying over sodium sulphate, filtration and concentration there is obtained (all-E)-6,10-dimethyl-12-[tetrahydro-2H-pyran-2-yl)oxy]-1,6,10-dodecatrien-3-ol in the form of a yellowish oil.

(b) A mixture of 11.2 g (36 mmol) of the crude (all-E)-6,10-dimethyl-12-[(tetrahydro-2H-pyran-2-yl)oxy]-1,6,10-dodecatrien-3-ol obtained, 50 g of manganese dioxide (active precipitated) and 500 ml of methylene chloride is stirred at room temperature. After in each case a few hours the mixture is filtered and treated with manganese dioxide. After a total of 30 hours and a four-fold treatment with fresh manganese dioxide the mixture is filtered over a Hyflo layer and the filtrate is evaporated. As the residue there remains behind crude (all-E)-6,10-dimethyl-12-[(tetrahydro-2H-pyran-2-yl)oxy]-1,6,10-dodecatrien-3-one in the form of a yellow oil; this is dissolved in 750 ml of 90% ethanol, 1.2 g of pyridinium toluene-4-sulphonate are added thereto and the mixture is stirred at 55° for 3.5 hours. The mixture is then concentrated, the residue is taken up in ether and washed with ice-water. The organic phase is washed firstly with saturated sodium hydrogen carbonate solution and then with saturated sodium chloride solution, dried over sodium sulphate, filtered and concentrated. The residue is chromatographed on silica gel with hexane-ethyl acetate 2:1, whereby (all-E)-12-hydroxy-6,10-dimethyl-1,6,10-dodecatrien-3-one is obtained as a colourless oil. MS; 195 (M—C$_2$H$_3$)$^+$, 189 (M—(H$_2$O+CH$_3$))$^+$.

EXAMPLE 56

(a) A mixture of 2.4 g (100 mmol) of magnesium, 100 ml of absolute tetrahydrofuran and about 100 mg of iodine is heated to reflux temperature in an argon atmosphere. After the iodine colour has disappeared 12.0 g (89 mmol) of (Z)-2-bromo-2-butene are added dropwise thereto. The mixture is then boiled at reflux for 2.5 hours. After cooling to room temperature the mixture is filtered through glass wool in a stream of argon. The Grignard solution obtained is subsequently cooled to −10° and treated dropwise with 12.0 g (43 mmol) of (all-E)-4,8-dimethyl-10-[(tetrhydro-2H-pyran-2-yl)oxy]-4,8-decadienal. After completion of the addition the mixture is stirred at 15° for a further 20 hours. The mixture is then treated with saturated ammonium chloride solution and subsequently extracted twice with ether. The combined organic phases are dried over magnesium sulphate, filtered and concentrated. The residue is chromatographed on silica gel with hexane-ethyl acetate 9:1, whereby there is obtained (7E,11E)-3,7,11-trimethyl-13-[(tetrahydro-2H-pyran-2-yl)oxy]-2,7,11-tridecatrien-4-ol in a 2Z:2E ratio of 89%:11% (GC and $^1$H-NMR). MS: 234 (M-(2-hydroxy-tetrahydropyran, $C_5H_{10}O_2$))+.

(b) A mixture of 4.5 g (13.3 mmol) of the (2(Z/E),-7E,11E)-3,7,11-trimethyl-13-[(tetrahydro-2H-pyran-2-yl)oxy]-2,7,11-tridecatrien-4-ol obtained, 130 ml of methanol and 7.0 g strongly acidic ion-exchanger (Dowex 50 W 8 X) is stirred at room temperature for 3 hours. After filtration and concentration of the filtrate the residue is chromatographed on silica gel (0.043–0.060 mm) with hexane-ethyl acetate 1:1 under a pressure of about 0.1 bar of compressed air, whereby there is obtained (2E,6E)-3,7,11-trimethyl-2,6,11-tridecatriene-1,10-diol in a 11Z:11E ratio of 90%:10% (GC and $^{13}C$-NMR). MS: 178 (M—($C_4H_8$+$H_2O$))+.

EXAMPLE 57

(a) A mixture of 10 g (29.7 mmol) of (2(Z/E),7E,1-1E)-3,7,11-trimethyl-13-[(tetrahydro-2H-pyran-2-yl)oxy]-2,7,11-tridecatrien-4-ol, 350 ml of methylene chloride and 150 g of manganese dioxide (active, precipitated) is stirred at room temperature for 4 days. After filtration over a Hyflo layer and concentration of the filtrate the residue is chromatographed on silica gel (0.043–0.060 mm) with hexane-ethyl acetate 80:20 under a pressure of about 0.1 bar of compressed air, whereby in addition to unreacted starting material there is obtained (2(E/Z)-,7E,11E)-3,7,11-trimethyl-13-[(tetrahydro-2H-pyran-2-yl)oxy]-2,7,11-tridecatrien-4-one. The 2(E/Z) ratio amounts to about 25%:5% in accordance with gas chromatography and $^{13}C$—NMR. MS: 249 (M-tetrahydropyran, $C_5H_8O$)+, 232 (M-(2-hydroxy-tetrahydropyran, $C_5H_{10}O_2$))+.

(b) A solution of 2.2 g (6.5 mmol) of (2(E/Z),7E,1-1E)-3,7,11-trimethyl-13-[(tetrahydro-2H-pyran-2-yl)oxy]-2,7,11-tridecatrien-4-one is added dropwise at room temperature to a suspension of 4 g of strongly acidic ion-exchanger (Dowex 50 W 8 X) in 100 ml of methanol. The mixture is subsequently stirred at room temperature for a further 2 hours. After filtration and evaporation of the filtrate the residue is chromatographed on silica gel with hexane-ethyl acetate 1:1 under a pressure of about 0.1 bar of compressed air, whereby (2(E/Z)-,7E,11E)-13-hydroxy-3,7,11-trimethyl-2,7,11-tridecatrien-4-one is obtained as a slightly yellowish oil. The 2Z:2E ratio amounts to 61.5%:38.5% in accordance with gas chromatography and $^1$H-NMR. MS (CI with $NH_3$): 233 ((M+H)—$H_2O$))+.

EXAMPLE 58

(a) 10 g (84 mmol) of cyclopropyl bromide are added dropwise at 0° to 1.2 g (172 mmol) of metallic lithium in 100 ml of absolute ether. The mixture is subsequently stirred at room temperature for 90 minutes. After filtering off the excess lithium the filtrate is cooled to −70° and treated dropwise with 20 g (76.4 mmol) of (all-E)-4,8-dimethyl-10-[(tetrahydro-2H-pyran-2-yl)oxy]-4,8-dodecadienal. The mixture is left to warm slowly to room temperature and is then stirred for a further 20 minutes. The mixture is subsequently cooled to 0°, treated with 100 ml of saturated ammonium chloride solution and extracted twice with ether. The combined ether phases are dried over sodium sulphate, filtered and concentrated. The residue is chromatographed on silica gel with hexane-ethyl acetate 9:1, whereafter there is obtained α-[(all-E)-3,7-dimethyl-9-[(tetrahydro-2H-pyran-2-yl)oxy]-3,7-nonadienyl]cyclopropanemethanol. MS: 238 (M-dihydropyran, $C_5H_8O$)+.

(b) A mixture of 2.5 g (7.75 mmol) of α-[(all-E)-3,7-dimethyl-9-[(tetrahydro-2H-pyran-2-yl)oxy]-3,7-nonadienyl]cyclopropanemethanol, 50 ml of 90% ethanol and 187 mg of pyridinium toluene-4-sulfonate is stirred at 50° for 6 hours. The mixture is evaporated and the residue is taken up in ether and washed with water. After extraction of the aqueous phase with ether the combined ether phases are dried over sodium sulphate, filtered and concentrated. The resiude is chromatographed on silica gel with hexane-ethyl acetate 9:1, whereafter there is obtained (all-E)-10-cyclopropyl-3,7-dimethyl-2,6-decadiene-1,10-diol. MS: 220 (M—$H_2O$)+.

EXAMPLE 59

(a) A mixture of 10 g (31 mmol) of α-[(all-E)-3,7-dimethyl-9-[(tetrahydro-2H-pyran-2-yl)oxy]-3,7-nonadienyl]cyclopropanemethanol, 500 ml of methylene chloride and 200 g of manganese dioxide (active, precipitated) is stirred at room temperature for 6 hours. After filtration over sodium sulphate and evaporation of the filtrate the resiude is chromatographed on silica gel with hexane-ethyl acetate 9:1, whereafter there is obtained (all-E)-1-cyclopropyl-4,7-dimethyl-10-[(tetrahydro-2H-pyran-2-yl)oxy]-4,8-decadien-1-one. MS: 236 (M-dihydropyran, $C_5H_8O$)+.

(b) A mixture of 3.3 g (10.3 mmol) of (all-E)-1-cyclopropyl-4,7-dimethyl-10-[(tetrahydro-2H-pyran-2-yl)oxy]-4,8-decadien-1-one, 60 ml of ethanol and 241 mg of pyridinium toluene-4-sulfonate is stirred at 50° for 1 hour. The reaction mixture is then concentrated, the residue is taken up in ether and washed with water. After extraction of the aqueous phase with ether the combined ether phases are dried over sodium sulphate, filtered and concentrated. The residue is chromatographed on silica gel with hexane-ethyl acetate 8:2. There is obtained (all-E)-1-cyclopropyl-4,8-dimethyl-10-hydroxy-4,8-decadien-1-one. MS: 218 (M—$H_2O$)+.

EXAMPLE 60

4.2 g (36 mmol) of (E/Z)-1-bromo-1-propene are added dropwise to a warmed mixture of 1.7 g (72 mmol) of magnesium shavings, 50 ml of tetrahydrofuran previously distilled over sodium and a crystal of iodine at such a rate that the reaction mixture is held just a boiling. After completion of the addition the mixture is boiled under reflux for a further 1 hour. After cooling solid constituents are filtered off in an argon atmosphere. The Grignard solution, cooled to 0°, is subsequently treated dropwise within 15 minutes with a solution of 5 g (18 mmol) of (all-E)-4,8-dimethyl-10-[tetrahydro-2H-pyran-2-yl)oxy]-4,8-decadienal in 5 ml of absolute tetrahydrofuran. The mixture is subsequently stirred at 0° for a further 1 hour and at room temperature for 4 hours. The reaction mixture is then poured into 150 ml of saturated ammonium chloride solution and extracted three times with ether. The combined organic phases are washed firstly with saturated sodium hydrogen carbonate solution and then with saturated sodium chloride solution, subsequently dried over sodium sulphate, filtered and evaporated.

The (2(E/Z),7E-,11E)-7,11-dimethyl-13-[tetrahydro-2H-pyran-2-yl)oxy]-2,7,11-tridecatrien-4-ol which remains behind as the residue is stirred at room temperature for 3 hours together with 100 ml of methanol and 10 g of strongly acidic ion-exchanger (Dowex 50 W 8 X). After filtration and concentration the residue is chromatographed on silica gel with hexane-ethyl acetate 1:1, whereafter there is obtained (2E,6E,11(E/Z))-3,7-dimethyl-2,6,11-tridecatriene-1,10-diol in a E:Z ratio of 83:17 (GC). MS (CI with NH$_3$): 238 ((M+NH$_4$)—H$_2$O)$^+$, 221 ((M+H)—H$_2$O)$^+$, 220 ((M+NH$_4$)—2H$_2$O)$^+$, 203 ((M+H)—2H$_2$O)$^+$.

EXAMPLE 61

(a) A mixture of 1.79 g (56 mmol) of (2(E/Z),7E,11E)-7,11-dimethyl-13-[(tetrahydro-2H-pyran-2-yl)oxy]-2,7,11-tridecatrien-4-ol, prepared according to the details in Example 61 and chromatographed on silica gel with hexane-ethyl acetate 4:1 with the addition of 0.1% triethylamine, 400 ml of methylene chloride and 100 g of manganese dioxide (active, precipitated) is stirred at room temperature. After a reaction period of in each case a few hours the mixture is filtered and fresh manganese dioxide is added thereto. In total fresh manganese dioxide is added four times over a reaction period of 5 days. The reaction mixture is then filtered through a mixture of Hyflo and sodium sulphate and the filtrate is evaporated. The yellowish oil which remains behind as the residue is chromatographed on silica gel with hexane-ethyl acetate 4:1 with the addition of 0.1% triethylamine, whereafter there is obtained (all-E)-7,11-dimethyl-13-[(tetrahydro-2H-pyran-2-yl)oxy]-2,7,11-tridecatrien-4-one as a colourless oil. IR (film): 1693 (ketone conj.), 1620 (—C=C—, conj.), 974 (—CH=CH—, trans).

(b) A mixture of 10 0 g (30 mmol) of (all-E)-7,11-dimethyl-13-[(tetrahydro-2H-pyran-2-yl)oxy]-2,7,11-tridecatrien-4-one, 250 ml of ethanol, 50 ml of water and 2.0 g of pyridinium toluene-4-sulfonate is stirred at 55° for 3 hours. The mixture is then evaporated, the residue is treated with 100 ml of toluene, again concentrated, 500 ml of ether are added thereto and the mixture is filtered through a layer of silica gel. The filtrate is concentrated and the residue, which remains behind in the form of a yellowish oil, is chromatographed on silica gel with hexane-ethyl acetate 2:1. There is obtained (all-E)-13-hydroxy-7,11-dimethyl-2,7,11-tridecatrien-4-one as a colourless oil MS: 205 (M—CH$_2$OH)$^+$.

EXAMPLE 62

A solution of 2 g (20 mmol, 2.82 ml) of trimethylsilylacetylene in 40 ml of absolute tetrahydrofuran is treated dropwise at −70° with 12.5 ml (20 mmol) of a 1.6 molar solution of butyllithium in hexane. After completion of the addition the mixture is stirred at −70° fo a further 30 minutes, whereupon a solution of 5 g (17.8 mmol) of (all-E)-4,8-dimethyl-10-[(tetrahydro-2H-pyran-2-yl)-oxy]-4,8-decadienal in 40 ml of absolute tetrahydrofuran is added dropwise within 15 minutes. The reaction mixture is subsequently stirred at −70° C. for a further 30 minutes and is then poured into 500 ml of an ice-cold, saturated ammonium chloride solution. After three-fold extraction with hexane the combined organic phases are dried over sodium sulphate, filtered and concentrated, whereafter there is obtained crude (all-E)-6,10-dimethyl-12-[(tetrahydro-2H-pyran-2-yl)oxy]-1-(trimethylsilyl)-6,10-dodecadien-1-yn-3-ol.

This material is added dropwise at 0° within 15 minutes to a suspension of 63 g of manganese dioxide (active, precipitated). The mixture is subsequently stirred at 0° for a further 4 hours. After filtration over sodium sulphate and concentration there is obtained crude (all-E)-6,10-dimethyl-12-[(tetrahydro-2H-pyran-2-yl)oxy]-1-(trimethylsilyl)-6,1-dodecadien-1-yn-3-one.

3.8 g (10 mmol) of this material are stirred at 55° for 1 hour together with 800 mg of pyridinium toluene-4-sulfonate and 100 ml of ethanol. After concentration the residue is chromatographed on silica gel with hexane-ethyl acetate 9:1 under a pressure of about 0.1 bar of compressed air, whereafter there is obtained (all-E)-12-hydroxy-6,10-dimethyl-1-(trimethylsilyl)-6,10-dodecadien-1-yn-3-one. MS: 261 (M—CH$_2$OH)$^+$, 259 (M—(CH$_3$+H$_2$O)$^+$.

EXAMPLE 63

4.57 g (20.7 mmol) of (all-E)-12-hydroxy-6,10-dimethyl-6,10-dodecadien-1-yn-3-one are added dropwise at room temperature within 10 minutes to a mixture of 11.4 g (140 mmol) of anhydrous sodium acetate, 29 g (0.2 mmol) of sodium sulphate, 10.85 g (0.13 mmol) of O-methylhydroxylamine hydrochloride and 110 ml of absolute methanol. The reaction mixture is then heated to 66°–68° and stirred for 1 hour. The mixture is then left to cool, filtered, the filtrate is concentrated and the residue is taken up in 500 ml of distilled water. The mixture is then extracted twice with ether, whereupon the combined extracts are washed with saturated sodium chloride solution and subsequently filtered over sodium sulphate. After concentrating the filtrate the residue is chromatographed on silica gel with hexane-ethyl acetate 2:1. There is obtained (6E,10E)-12-hydroxy-6,10-dimethyl-6,10-dodecadien-1-yn-3-one (E/Z)-O-methyl oxime; the E/Z ratio amounts to about 1:2 in accordance with GC and NMR. MS: 216 (M—OCH$_3$)$^+$.

EXAMPLE 64

A mixture of 12 g (37.2 mmol) of (all-E)-3,7,11-trimethyl-10-[(tetrahydro-2H-pyran-2-yl)oxy]-2,6,11-dodecatrien-1-ol, 120 g of manganese dioxide and 500 ml of hexane is stirred at room temperature for 1 hour. The mixture is then filtered over silicons earth, the filtrate is concentrated and the residue is chromatographed on silica gel with hexane-ethyl acetate with the addition of 0.1% of a 25% ammonia solution. There is obtained (all-E)-3,7,11-trimethyl-10-[(tetrahydro-2H-pyran-2-yl)oxy]-2,6,11-dodecatrienal. MS: 218 (M-(2-hydroxy-tetrahydropyran, C$_5$H$_{10}$O$_2$))$^+$.

(b) 48.7 ml (78 mmol) of a 1.6M solution of butyllithium in hexane are added dropwise to 100 ml (0.15 mmol) of an about 1.5M solution of propyne in abs. tetrahydrofuran. After stirring at −70° for 1 hour a solution of 7.25 g (22.6 mmol) of (all-E)-3,7,11-trimethyl-10-[(tetrahydro-2H-pyran-2-yl)oxy]-2,6,11-dodecatrienal in 100 ml of absolute tetrahydrofuran is added dropwise at the same temperature, whereupon the mixture is stirred at −70° for a further 30 minutes. The reaction mixture is then poured slowly into 500 ml of an ice-cold saturated ammonium chloride solution, whereupon the mixture is shaken vigorously. After three-fold extraction with ether the combined organic phases are dried over sodium sulphate and concentrated. The residue is chromatographed on silica gel with hexane-ethyl acetate 4:1 with the addition of 0.1% triethylamine. There is obtained (all-E)-6,10,14-trimethyl-13-[(tetrahydro-2H-pyran-2-yl)oxy]-5,9,14-pentadecatrien-2-yn-4-ol. IR (film): 3427 (OH), 2232 (—C≡C—), 1135, 1116, 1076 (—C—O—C—).

(c) A suspension of 62 g manganese dioxide (active, precipitated) in 200 ml of methylene chloride is treated at 0° with 6.12 g (17.1 mmol) of (all-E)-6,10,14-trimethyl-13-[(tetrahydro-2H-pyran-2-yl)oxy]-5,9,14-pentadecatrien-2-yn-4-ol. After warming to room temperature the mixture is stirred for a further 45 minutes. The mixture is then filtered over sodium sulphate and the filtrate is concentrated. The (5(E/Z),9E)-6,10,14-trimethyl-13-[(tetrahydro-2H-pyran-2-yl)oxy]-5,9,14-pentadecatrien-2-yn-4-one which remains behind as the residue is stirred at 55° for 20 hours together 450 mg of pyridinium toluene-4-sulfonate and 80 ml of 90% ethanol. The mixture is then concentrated and the residue is taken up in ether. After two-fold washing with water the organic phase is washed once with saturated sodium chloride solution, filtered over sodium sulphate and concentrated. The residue is chromatographed on silica gel with hexane-ethyl acetate 4:1, whereafter there is obtained (5(E/Z,9E)-13-hydroxy-6,10,14-trimethyl-5,9,14-pentadecatrien-2-yn-4-one in a (E/Z) ratio of 2:1 (GC, NMR). MS: 241 (M—(CH$_3$+H$_2$O)+.

EXAMPLE 65

(a) 4.86 g of magnesium shavings, 100 mg of mercury(II) chloride and 100 ml of ether are placed under an argon atmosphere in a 500 ml sulfonation flask provided with a mechanical stirrer, a dropping funnel and a thermometer. The dropping funnel is charged with a solution of 23.8 g (15.1 ml) of propargyl bromide in 50 ml of ether and 1.0 ml of this solution is added dropwise to the above mixture at room temperature. After the reaction has begun the mixture is cooled to −20° and the remainder of the propargyl bromide solution is added dropwise within 3 hours so that the reaction temperature does not exceed −15°. After completion of the addition the mixture is stirred at −20° for a further 15 minutes. A solution of 28.0 g of (E,E)-4,8-dimethyl-10-[(tetrahyro-2H-pyran-2-yl)-oxy]-4,8-decadienal in 50 ml of ether is then added dropwise at 0°. After the addition of half of this solution a precipitate results, whereupon 100 ml of ether and 100 ml of tetrahydrofuran are added in order to facilitate the stirring. The remainder of the mentioned solution is subsequently added dropwise at 5°–10° and the resulting grey suspension is stirred overnight in a melting ice-bath and then poured into a mixture of ice and saturated ammonium chloride solution. The organic phase is separated and the aqueous phase is extracted twice with hexane. The combined organic phases are washed with saturated ammonium chloride solution, saturated sodium bicarbonate solution and saturated sodium chloride solution, dried over sodium sulphate, filtered and evaporated. The residue is chromatographed on 1.0 kg of silica gel with hexane-ethyl acetate 10%→25%. There is obtained (E,E)-7,11-dimethyl-13-[(tetrahydro-2H-pyran-2-yl)oxy]-7,11-tridecadien-trien-1-yn-4-ol as a yellow oil. IR (film): 3450 (OH); 3307, 2118 (—C≡C—H); 1667 (C=C). MS: 236 (1, (M-dihydro-pyran, C$_5$H$_8$O)+); 218 (0,5, (M-(2-hydroxytetrahydro-pyran, C$_5$H$_{10}$O$_2$))+); 85 (100, C$_5$H$_9$O+).

(b) A solution of 6.40 g of (E,E)-7,11-dimethyl-13-[(tetrahydro-2H-pyran-2-yl)oxy]-7,11-tridecadien-1-yn-4-ol and 1.50 g of pyridinium toluene-4-sulfonate in 200 ml of abs. ethanol is heated to 60° under argon for 2.5 hours. The reaction mixture is cooled and evaporated, and the residue is taken up in ether and water. After separating the organic phase the aqueous phase is extracted twice with ether and the combined organic phases are washed with 2N hydrochloric acid, saturated sodium carbonate solution and saturated sodium chloride solution, dried over sodium sulphate, filtered and evaporated. The yellow oil which remains behind as the residue is chromatographed on 400 g of silica gel, with elution being carried with hexane-ethyl acetate 25%→40%. In this manner there is obtained (E,E)-3,7-dimethyltrideca-2,6-dien-12-yn-1,10-diol as a yellowish oil. IR (film); 3350 (OH); 3305, 2118 (—C≡CH); 1667 (C=C); 1003, (OH). MS: 205 (1, (M—CH$_2$OH)+); 203 (1, M—H$_2$O—CH$_3$)+); 105 (100); 93 (100).

EXAMPLE A

Crystalline compounds of formula I can be used as active substances for the manufacture of hard gelatine capsules, the content of which has the following composition per capsule:

| | |
|---|---|
| Active substance | 50–250.0 mg |
| Lactose powd. | 40.0 mg |
| Lactose cryst. | 230–30.0 mg |
| Maize starch white | 20.0 mg |
| Talc | 8.0 mg |
| Magnesium stearate | 2.0 mg |
| Fill weight per capsule | 250.0 mg |

The active substance and the adjuvants are mixed with one another and the mixture is filled into hard gelatine capsules of suitable size. If required, the capsules are subsequently provided with a gastric juice-resistant coating consisting of hydropropylmethylcellulose phthalate.

EXAMPLE B

Non-crystalline compounds of formula I can be used as described hereinafter as active substances for the manufacture of soft gelatine capsules; the abbreviations used have the following significance:

| | | |
|---|---|---|
| BHA | = | Butylated hydroxyanisole |
| BHT | = | Butylated hydroxytoluene |
| PEG | = | Polyethylene glycol |

(a) 0.2 mg of BHA and 1.0 mg of ascorbyl palmitate are dissolved in 400 ml of PEG 400 at room temperature under a nitrogen atmosphere. The solution is treated with 50–250 mg of active substance at room temperature under nitrogen. After all has dissolved the mixture obtained is filled in liquid form into soft gelatine capsules.

(b) 300 mg of PEG 400 and 100 mg of PEG 4000 are warmed under nitrogen until the mixture has liquefied. Thereafter, 0.1 mg of BHA, 0.1 mg of BHT and 1.0 mg of ascorbyl palmitate are added thereto under nitrogen. After all has dissolved 50–250 mg of active substance are added under nitrogen and dissolved while mixing thoroughly. The liquid is then filled into soft gelatine capsules.

(c) 0.2 mg of BHA, 0.2 mg of BHT and 1.0 mg of ascorbyl palmitate are dissolved in 400 ml of Polysorbate-80 at room temperature under nitrogen. The mixture is treated with 50–250 mg of active substance under nitrogen. After all has dissolved the liquid is filled into soft gelatine capsules.

(d) A mixture of in each case 200 mg of Polysorbate-60 and Polysorbate-80 is warmed. The liquid mixture obtained is treated under nitrogen with 0.2 mg of BHA, 1.0 mg of α-tocopherol and 2.0 mg of ascorbyl palmitate. After all has dissolved 50-250 mg of active substance are added under nitrogen. After mixing thoroughly until solution is complete the mixture obtained is filled into soft gelatine capsules.

We claim:

1. Compounds of the general formula

wherein
R¹ is

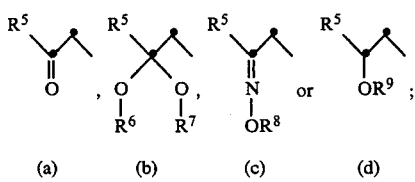

one of R² and R³ is $(C_1-C_8)$-alkyl and the other is hydrogen or $(C_1-C_8)$-alkyl;
R⁴ is a

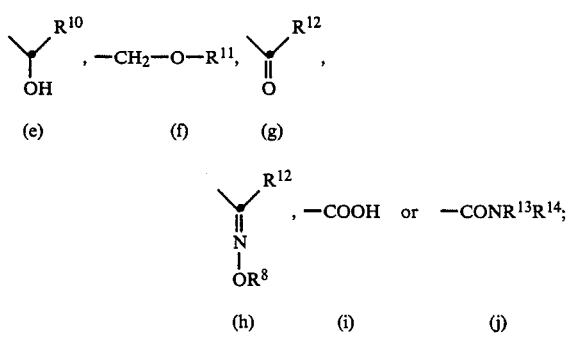

R⁵ is a $(C_2-C_8)$-alkyl, other than isopropyl, $(C_3-C_8)$-cycloalkyl, $(C_2-C_8)$-alkenyl, $(C_2-C_8)$-alkynyl, tri-$(C_1-C_8)$-alkyl-silyl-ethynyl or, when R¹ is (a), R⁵ can also be

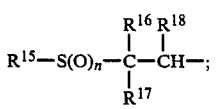

R⁶ and R⁷ are individually $(C_1-C_8)$-alkyl or taken together form a di- or trimethylene group optionally substituted by one or two $(C_1-C_8)$-alkyl, $(C_1-C_8)$-alkoxy-$(C_1-C_8)$-alkyl or $(C_1-C_8)$-alkoxycarbonyl groups;
R⁸ is hydrogen or $(C_1-C_8)$-alkyl;
R⁹ is hydrogen or $(C_2-C_8)$-alkanoyl;
R¹⁰ is $(C_1-C_8)$-alkyl;
R¹¹ is hydrogen, $(C_1-C_8)$-alkyl, $(C_2-C_8)$-alkanoyl or

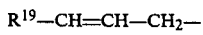

or

R¹² is hydrogen, $(C_1-C_8)$-alkyl, $(C_2-C_8)$-alkenyl or $(C_2-C_8)$-alkynyl;
R¹³ and R¹⁴ are individually hydrogen or $(C_1-C_8)$-alkyl or taken together with the attached nitrogen atom form 1-pyrrolidinyl, piperidino or morpholino;
R¹⁵ is $(C_1-C_8)$-alkyl, $(C_2-C_8)$-alkanoyl, $(C_1-C_8)$-alkoxycarbonyl-$(C_1-C_8)$-alkyl, hydroxy-$(C_2-C_8)$-alkyl, $(C_2-C_8)$-alkanoyloxy-$(C_2-C_8)$-alkyl, $(C_2-C_8)$-alkanoylamino-$(C_2-C_8)$-alkyl or $(C_2-C_8)$-alkyl disubstituted by $(C_2-C_8)$-alkanoylamino and $(C_1-C_8)$-alkoxycarbonyl or by $(C_2-C_8)$-alkanoyloxy and $(C_1-C_8)$-alkoxycarbonyl;
n is the number 0, 1 or 2;
R¹⁶, R¹⁷ and R¹⁸ individually are hydrogen or $(C_1-C_8)$-alkyl containing in total a maximum of 6 C-atoms;
R¹⁹ is hydrogen or $(C_1-C_5)$-alkyl;
each of the dotted lines designates an optional additional C—C bond having the E- or Z-configuration; and
the double bond present in the residues of formulae (c) and (h) has the E- or Z-configuration;
as well as pharmaceutically acceptable salts of acidic compounds of formula I with bases, with the exception of 10-hydroxy-3,7,11-trimethyl-2,6,11-dodecatrienoic acid and 3,7,11-trimethyl-2,6,11-dodecatriene-1,10-diol.

2. The compound of claim 1, wherein R¹ is a residue of formula (a), (b), (c) or (d), R² and R³ individually are $(C_1-C_8)$-alkyl, R⁴ is a residue of formula (f), (g), (h), (i) or (j), R⁵ is $(C_2-C_8)$-alkenyl, $(C_2-C_8)$-alkynyl or tri-$(C_1-C_8)$-alkyl-silyl-ethynyl, R⁶ and R⁷ are individually $(C_1-C_8)$-alkyl or taken together form the dimethylene; R⁸ is hydrogen or $(C_1-C_8)$-alkyl, R⁹ is hydrogen, R¹¹ is hydrogen or $(C_2-C_8)$-alkanoyl, R¹², R¹³ and R¹⁴ are hydrogen and two of the dotted lines designate nonconjugated additional C—C bonds.

3. The method of claim 2, wherein R² and R³ are methyl, R⁵ is vinyl, 1-methylvinyl, 1-propenyl, 2-methyl-1-propenyl, ethynyl, 1-propynyl or trimethylsilylethynyl, R⁶ and R⁷ are individually methyl or ethyl or taken together from dimethylene group, R⁸ is hydrogen or methyl and R¹¹ is hydrogen or acetyl.

4. The compound of claim 2, wherein R¹ is (a), (b) or (c).

5. The compound of claim 1 wherein said compound has the formula:

wherein R¹ is as above; R³¹, is hydrogen, alkyl, —CH₂—C≡CH, or —CH₂—CH=CH₂.

6. The compound of claim 5 wherein R₁ is

7. The compound of claim 6 wherein R₅ is alkenyl.

8. The compound of claim 7 wherein said compound is (all-E)-12-hydroxy-6,10-dimethyl-1,6,10-dodecatrien-3-one.

9. The compound of claim 7 wherein said compound is (all-E)-12-hydroxy-2,6,10-trimethyl-1,6,10-dodecatrien-3-one.

10. The compound of claim 7 wherein said compound is (all-E)-13-hydroxy-7,11-dimethyl-2,7,11-tridecatrien-4-one.

11. The compound of claim 7 wherein said compound is (all-E)-13-hydroxy-2,7,11-trimethyl-2,7,11-tridecatrien-4-one.

12. The compound of claim 7 wherein said compound is (6E,10Z)-12-hydroxy-2,6,10-trimethyl-1,6,10-dodecatrien-3-one.

13. The compound of claim 7 wherein said compound is (6E,10E)-12-hydroxy-2,6,10-trimethyl-1,6,10-dodecatrien-3-one.

14. The compound of claim 7 wherein said compound is (6Z,10Z)-12-hydroxy-2,6,10-trimethyl-1,6,10-doecatrien-3-one.

15. The compound of claim 6 wherein R₅ is alkynyl.

16. The compound of claim 15 wherein said compound is (all-E)-12-Hydroxy-6,10-dimethyl-6,10-dodecadien-1-yne-3-one.

17. The compound of claim 14 wherein said compound is (all-E)-13-hydroxy-7,11-dimethyl-7,11-tridecadien-2-yne-4-one.

18. The compound of claim 5 wherein R¹ is

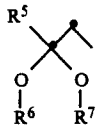

wherein R⁵, R⁶ and R⁷ are as above.

19. The compound of claim 18 where R⁵ is alkenyl.

20. The compound of claim 19 wherein said compound is (all-E)-3,7-dimethyl-9-[2-(1-methylvinyl)-1,3-dioxolan-2-yl]-2,6-nonadien-1-ol.

21. The compound of claim 19 wherein said compound is (all-E)-10,10-dimethoxy-3,7,11-trimethyl-2,6,11-dodecatrien-1-ol.

22. The compound of claim 18 wherein R⁵ is alkynyl.

23. The compound of claim 22 wherein said compound is (all-E)-10,10-diethoxy-3,7-dimethyl-2,6-dodecadien-11-yn-1-ol.

24. The compound of claim 18 wherein R₅ is trialkylsilylethynyl.

25. The compound of claim 24 wherein said compound is (all-E)-12-hydroxy-6,10-dimethyl-1-(trimethylsilyl)-6,10-dodecadien-1-yn-3-one.

26. The compound of claim 5 wherein R₁ is

wherein R⁵ is as above and R⁹ as shown above.

27. The compound of claim 26 wherein said compound is (2E,6E,11(E/Z))-3,7-dimethyl-2,6,11-tridecatriene-1,10-diol.

28. The compound of claim 6 wherein R⁵ is

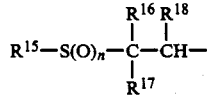

wherein R¹⁵, R¹⁶, R¹⁷, R¹⁸ and n are as above.

29. The compound of claim 28 wherein said compound is (6E,10Z)-12-hydroxy-1-(2-hydroxyethyl-)thio]-2,6,10-trimethyl 6,10-dodecadien-3-one.

30. The compound of claim 28 wherein said compound is (2Z,6E)-12-[(2-acetoxyethyl)thio]-3,7,11-trimethyl-2,6-dodecadienyl acetate.

31. The compound of claim 28 wherein said compound is methyl [(6E,10Z)-12-hydroxy-2,6,10-trimethyl-3-oxo-6,10-dodecadienyl]thio]acetate.

32. The compound of claim 5 wherein R¹ is

wherein R⁵ and R⁸ are as above.

33. The compound of claim 32 wherein said compound is (6E,10E)-12-hydroxy-6,10-dimethyl-6-10-dodecadien-1-yn-3-one (E/Z)-O-methyloxime.

34. The compound of claim 32 wherein said compound is (6E,10E)-12-hydroxy-2,6,10-trimethyl-1,6,10-dodecatrien-3-one-oxime.

35. The compound of claim 1 wherein said compound has the formula:

wherein R¹ and R¹² are as above.

36. The compound of claim 35 wherein R¹ is

37. The compound of claim 36 wherein said compound is (all-E)-10-oxo-3,7,11-trimethyl-2,6,11-dodecatrienal.

38. The compound of claim 35 wherein R¹ is

wherein R⁵ and R⁹ are as above.

39. The compound of claim 38 wherein said compound is (all-E)-10-hydroxy-3,7,11-trimethyl-2,6,11-dodecatrienal.

40. The compound of claim 1 wherein said compound has the formula:

wherein R¹ is as above.

41. The compound of claim 40 wherein R¹ is

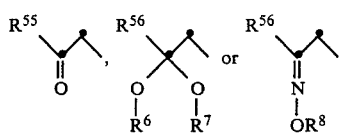

wherein R⁶, R⁷ and R⁸ is as above; and R⁵⁶ is cycloalkyl, alkenyl, alkynyl, trialkylsilylethynyl, and R⁵⁵ is alkenyl, cycloalkyl, alkynyl, or trialkylsilylethynyl.

42. The compound of claim 41 wherein said compound is (all-E)-10-oxo-3,7,11-trimethyl-2,6,11-dodecatrienoic acid.

43. The compound of claim 1 wherein said compound has the formula:

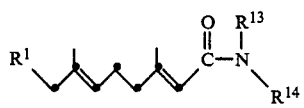

wherein R¹, R¹³ and R¹⁴ as above.

44. The compound of claim 43 wherein R¹ is

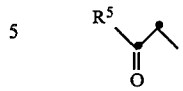

and R⁵ is as above.

45. The compound of claim 43 wherein said compound is (E,E)-3,7,11-trimethyl-10-oxo-2,6,11-dodecatrien-amide.

46. The compound of claim 44 wherein R⁵ is

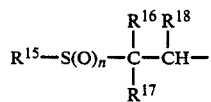

wherein n, R¹⁵, R¹⁶, R¹⁷ and R¹⁸ are as above.

47. The compound of claim 46 wherein said compound is (2E,6E)-12[(2-hydroxyethyl)sulfinyl]-3,7,11-trimethyl-10-oxo-2,6-dodecadienamide.

* * * * *

UNITED STATES PATENT AND TRADEMARK OFFICE
CERTIFICATE OF CORRECTION

PATENT NO. : 4,827,004
DATED : May 2, 1989
INVENTOR(S) : Albert Fischli, Max Schmid, Rudolf Schmid It is certified that error appears in the above-identified patent and that said Letters Patent is hereby corrected as shown below:

Column 52 line 38 "method" should be --compound--

Signed and Sealed this

Third Day of October, 1989

*Attest:*

DONALD J. QUIGG

*Attesting Officer*  *Commissioner of Patents and Trademarks*